United States Patent
Obikane et al.

(10) Patent No.: US 11,022,789 B2
(45) Date of Patent: Jun. 1, 2021

(54) OBSERVATION IMAGING APPARATUS

(71) Applicant: TAMRON CO., LTD., Saitama (JP)

(72) Inventors: Yasuhiko Obikane, Saitama (JP); Yoshito Iwasawa, Saitama (JP); Yuichi Imamiya, Saitama (JP); Yuri Koyama, Saitama (JP)

(73) Assignee: TAMRON CO., LTD., Saitama (JP)

(*) Notice: Subject to any disclaimer, the term of this patent is extended or adjusted under 35 U.S.C. 154(b) by 0 days.

(21) Appl. No.: 16/553,940

(22) Filed: Aug. 28, 2019

(65) Prior Publication Data
US 2020/0285041 A1    Sep. 10, 2020

(30) Foreign Application Priority Data

Mar. 4, 2019   (JP) .............................. JP2019-038701

(51) Int. Cl.
| G02B 23/24 | (2006.01) |
| A61B 1/05 | (2006.01) |
| H04N 5/225 | (2006.01) |
| G02B 13/00 | (2006.01) |
| G03B 37/00 | (2021.01) |

(52) U.S. Cl.
CPC ............ G02B 23/2407 (2013.01); A61B 1/05 (2013.01); G02B 13/003 (2013.01); H04N 5/2254 (2013.01); G03B 37/005 (2013.01)

(58) Field of Classification Search
CPC .... G02B 23/2407; G02B 13/003; A61B 1/05; H04N 5/2254; G03B 37/005
See application file for complete search history.

(56) References Cited

U.S. PATENT DOCUMENTS

| 2014/0218811 A1* | 8/2014 | Yamamoto | G02B 23/243 359/749 |
| 2014/0221749 A1* | 8/2014 | Grant | A61B 1/00103 600/112 |
| 2016/0120397 A1* | 5/2016 | Namii | G03B 37/005 348/68 |
| 2019/0246879 A1* | 8/2019 | Katakura | A61B 1/045 |
| 2019/0320885 A1* | 10/2019 | Inoue | G02B 23/04 |

FOREIGN PATENT DOCUMENTS

JP    2017-203972 A    11/2017

* cited by examiner

*Primary Examiner* — Richard A Hansell, Jr.
(74) *Attorney, Agent, or Firm* — Paratus Law Group, PLLC

(57) ABSTRACT

An observation imaging apparatus includes an insertion unit, an imaging lens, and an image sensor. The imaging lens is disposed in such a manner that an axial principal ray of an observation subject side surface of a lens is tilted with respect to a normal line passing through the center of gravity of a section of the insertion unit, the section passing through the center of an effective imaging range of the image sensor and having the smallest area. A point on the axial principal ray at which the distance between the normal line and the axial principal ray is smallest is located on the image side relative to the observation subject side surface of the lens and on the observation subject side relative to the image sensor. The observation imaging apparatus satisfies a predetermined conditional expression.

16 Claims, 10 Drawing Sheets

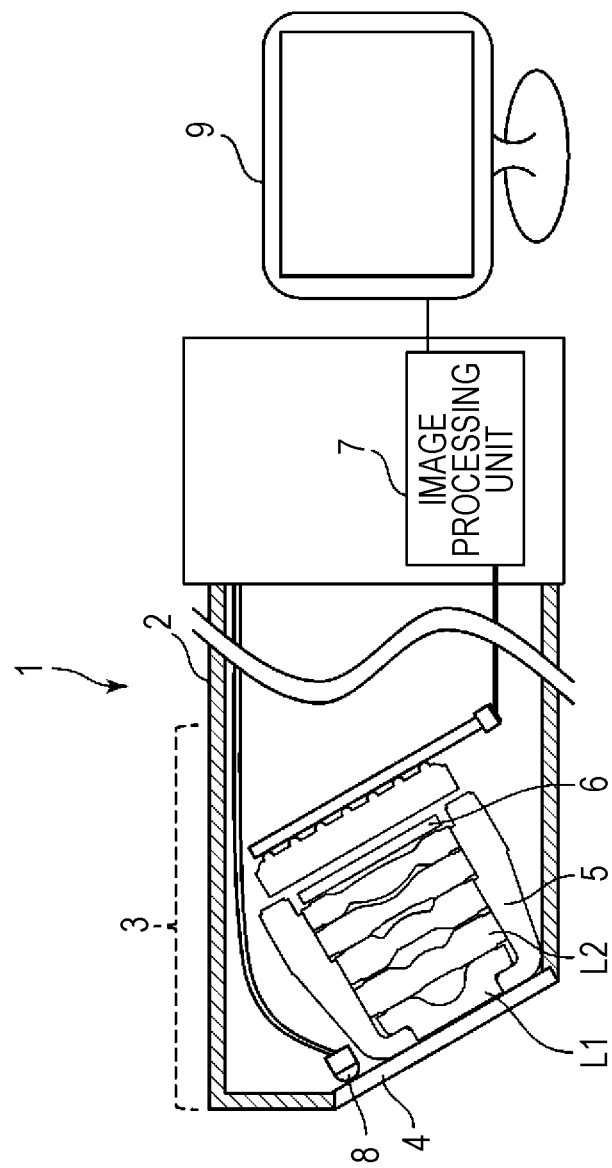

OBSERVATION IMAGING APPARATUS

CROSS-REFERENCE TO RELATED APPLICATIONS

This application is based on and claims the benefit of priority from Japanese Patent Application No. 2019-038701, filed on Mar. 4, 2019, the entire contents of which are incorporated herein by reference.

BACKGROUND OF THE INVENTION

Technical Field

The present invention relates to an observation imaging apparatus. In particular, the present invention relates to an observation imaging apparatus using a solid-state image sensor or the like, for example, an observation imaging apparatus suitable for observing the inside of a narrow space, such as an endoscope that observes the inside of a living body or an apparatus that observes the inside of a narrow space where a human cannot enter.

Related Art

In recent years, imaging apparatuses such as a digital still camera have become widespread, and increases in performance and pixel count of solid-state image sensors have also been making progress. Further, in recent years, increases in screen size and pixel count of image display apparatuses such as a monitor have also been making progress. Along with these progresses, observation systems in which a subject image acquired by an imaging apparatus is displayed on a large screen of an image display apparatus so that a lot of people can observe details of the subject image at the same time have also become widespread. The observation system is used, for example, in observation of the inside of a living body or a narrow space where the human cannot directly enter by inserting the observation system into the living body or the narrow space.

In such an observation system, a solid-state image sensor having an extremely high pixel count tends to be used. Thus, further higher performance and higher resolution are demanded also in an optical system. Further, since the insertion into a narrow space is required, downsizing and wider angle of an objective lens disposed on the most observation subject side are strongly demanded.

Thus, as an optical system used in such an observation system, JP 2017-203972 A proposes an optical system suitable for a rigid endoscope having a small size and a high performance. The optical system described in JP 2017-203972 A is provided with an objective lens which is housed in an insertion unit having a thin tubular shape. The optical system described in JP 2017-203972 A can be inserted into a narrow space such as the inside of a living body and satisfactorily observe the inside thereof using the small and wide angle objective lens.

However, JP 2017-203972 A is based on the premise that the insertion direction of the rigid endoscope and the observation direction of the optical system (an axial principal ray) are the same direction, and the field of view is fixed with respect to the insertion direction of the rigid endoscope. In order to achieve observation in an oblique direction with respect to the insertion direction, it is necessary for the optical system to correspond to a super wide angle, which, however, results in upsizing and increases in cost of the optical system.

Further, in JP 2017-203972 A, in order to achieve an optical system that satisfies a resolving power of 4K or 8K and has a long distance from the most observation subject side lens to the image sensor (has a long optical total length), a relay optical system and an imaging lens system are provided in addition to the objective lens so as to form an intermediate imaging plane in the optical system.

The present invention has been made in view of the above problems, and a principal object thereof is to provide an observation imaging apparatus that is capable of capturing an image in a desired field of view with respect to the insertion direction, has a high resolution, and a small size.

SUMMARY OF THE INVENTION

In order to solve the above problems, an observation imaging apparatus according to one aspect of the present invention includes: an insertion unit having a tubular shape; an imaging optical system disposed in a tip part of the insertion unit, having no intermediate imaging plane, and including one or more lenses; an image sensor configured to convert an optical image formed by the imaging optical system on an image side of the imaging optical system to an electric signal, in which when a normal line passing through a center of gravity of a cross section S of the insertion unit, the cross section S passing through a center of an effective imaging range of the image sensor and being perpendicular to an insertion direction of the insertion unit, is defined as a normal line A, the imaging optical system is fixed to the insertion unit in such a manner that an axial principal ray B of an observation subject side surface of a lens L1 disposed on the most observation subject side of the imaging optical system is tilted with respect to the normal line A, a point P on the axial principal ray B at which a distance between the normal line A and the axial principal ray B is smallest is located on the image side relative to the observation subject side surface of the lens L1 and on the observation subject side relative to the image sensor, and the observation imaging apparatus satisfies the following conditional expression:

$$0.10 < Dm/Ds < 0.80 \quad (1)$$

where

Dm is an area of the effective imaging range of the image sensor, and

Ds is an area of the cross section S.

According to the above aspect, it is possible to provide an observation imaging apparatus that is capable of capturing an image in a desired field of view with respect to the insertion direction, has a high resolution, and a small size.

BRIEF DESCRIPTION OF THE DRAWINGS

FIG. 1 is a diagram illustrating an example of an observation imaging apparatus according to an embodiment of the present invention;

DESCRIPTION OF THE EMBODIMENTS

First Embodiment

Figure 2A:
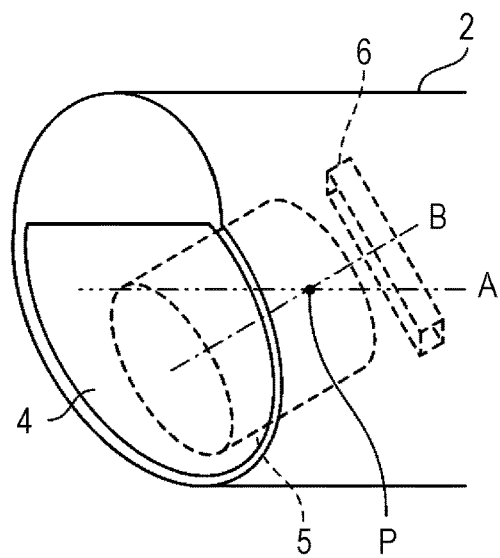
FIGS. 2A to 2C are diagrams schematically illustrating the disposition of an imaging lens in an insertion unit of the observation imaging apparatus according to the embodiment of the present invention.

An observation imaging apparatus according to an embodiment of the present invention will be described with reference to FIG. 1. FIG. 1 is a diagram illustrating an example of the observation imaging apparatus 1 according to the embodiment of the present invention. As illustrated in FIG. 1, the observation imaging apparatus 1 is provided with an insertion unit 2 having a tubular shape, an imaging lens (imaging optical system) 5 which is disposed in a tip part 3 of the insertion unit 2 and has no intermediate imaging plane, and an image sensor 6 which converts an optical image formed by the imaging lens on an image side of the imaging lens to an electric signal.

[Insertion Unit]

The insertion unit 2 has a tubular shape and a shape suitable for insertion into a narrow space for capturing an image of the narrow space. In the present embodiment, the insertion unit 2 is inserted into a narrow space. Thus, the insertion unit 2 is preferably a long and narrow tubular member extending in an insertion direction (length direction, axial direction) of the tube, and a smaller outer diameter of the tube is more preferred. For example, the insertion unit 2 preferably has a substantially cylindrical shape as a whole because the substantially cylindrical shape enables smooth insertion into a narrow space and reduces a load to the narrow space in contact with the insertion unit 2. However, the insertion unit 2 is not limited thereto. For example, the insertion unit 2 may be a tube whose section perpendicular to the insertion direction has an elliptical shape, a tube whose section has a polygonal shape such as a triangular shape or a quadrangular shape, or a tube whose section has a polygonal shape having tapered corners.

The tip part 3 of the insertion unit 2 is provided with a window 4 so as to enable the imaging lens 5 disposed inside the tip part 3 to capture an image of the outside of the insertion unit 2. In the present embodiment, the window 4 is made of glass, but not particularly limited thereto. The window 4 may be made of a transparent resin material.

The window 4 is preferably disposed substantially parallel to a plane perpendicular to an optical axis of an observation subject side surface of a lens L1 (first lens L1) which is disposed on the most observation subject side of the imaging lens 5 (described later). Such disposition of the window 4 can minimize distortion of light incident on the imaging lens 5.

Specifically, the outer diameter of the insertion unit 2 is preferably φ20 mm or less, more preferably φ15 mm or less, further more preferably φ12 mm or less, still further more preferably φ10 mm or less, still further more preferably φ8 mm or less, and still further more preferably φ6 mm or less. A smaller outer diameter enables easier insertion into a narrow space. In particular, in the case of application to an endoscope which is used in a surgery of the human body, a smaller outer diameter can reduce a burden on the human body.

Further, the configuration of the insertion unit 2 and the number of components which constitute the insertion unit 2 are not particularly limited to any configuration and any number. The insertion unit 2 may include one component or a plurality of components. When the insertion unit 2 includes a plurality of components, the tip part 3 may be removable together with the imaging lens 5 (described later), which is disposed in the tip part 3, from the insertion unit 2.

The length of the insertion unit 2 in the length direction is preferably long in view of expansion of a photographing scene. Specifically, the length L of the insertion unit 2 is preferably 100 mm or more, more preferably 300 mm or more, further more preferably 500 mm or more, still further more preferably 1000 mm or more, and still further more preferably 1500 mm or more.

[Imaging Lens]

The imaging lens 5 is disposed in the tip part 3 of the insertion unit 2. Further, the imaging lens 5 includes one or more lenses, and is configured to have no intermediate imaging plane in the lens system (configured not to form an imaging plane midway in the lens system).

In a conventional imaging apparatus such as a rigid endoscope, for example, an observation subject image intermediately formed by an objective lens is relayed through a relay lens system and then formed on an image sensor by an imaging lens to achieve a rigid endoscope having a long tubular shape while avoiding upsizing in the radial direction, as described in JP 2017-203972 A. However, in the conventional configuration, the cost is high due to a large number of lenses, and it is also difficult to expand an angle of view with respect to the insertion direction. In order to solve these problems, the objective lens needs to be a super wide angle lens or needs to include a reflecting member to change the angle of a ray of light. However, these countermeasures increase cost, and cannot avoid upsizing of the objective lens, which is not preferred in view of downsizing. Thus, the imaging lens 5 of the observation imaging apparatus 1 according to the present embodiment preferably has no intermediate imaging plane.

The number of lenses which constitute the imaging lens 5 is not particularly limited to any number. However, the imaging lens 5 preferably includes at least five lenses in terms of obtaining high optical performance. On the other hand, the number of lenses larger than eight hinders downsizing of the imaging lens in the full length direction. Thus, the number of lenses is preferably eight or less.

Further, the imaging lens 5 may be configured as a zoom lens capable of varying the focal length by two or more lens groups in which air spacing varies or may be configured as a fixed focal lens having a fixed focal length. In the present embodiment, an example in which the imaging lens 5 is a fixed focal lens will be described. Since the imaging lens 5 is disposed in the tip part 3 of the insertion unit 2 having a small outer diameter, the imaging lens 5 is preferably a fixed focal lens in terms of reducing the diameter of the insertion unit 2 and simplifying the configuration of the entire observation imaging apparatus 1.

The imaging lens 5 preferably includes no optical element having a reflecting surface as an optical element included in the imaging lens 5. The optical element having a reflecting surface indicates, for example, a mirror or a total reflection prism. Having no reflecting surface means that the imaging lens 5 includes an optical element such as a refractive lens, a diffractive lens, or a liquid crystal lens.

For example, in a case where the observation imaging apparatus 1 is an endoscope to be inserted into the human body, the tip part 3 that has once been inserted into the body is preferably replaced with a new tip part 3 when the observation imaging apparatus 1 is used again from a hygienic point of view. However, when a prism which changes the angle of the optical axis is disposed, the imaging lens 5 becomes expensive. Thus, it is difficult to replace the tip part 3 every time the tip part 3 is used. In this case, it is necessary to perform cleaning and sterilization by boiling every time the tip part 3 is inserted. Further, when sterilization by boiling is performed, it is difficult to use a resin lens which is sensitive to heat. Thus, the imaging lens 5 becomes more expensive. Thus, the imaging lens 5 including no prism can reduce its cost, and can reduce its cost even when the tip part 3 is replaced every time the tip part 3 is used. Further, replacing the tip part 3 every time the tip part 3 is used eliminates the necessity of sterilization by boiling. Thus, it is possible to use a resin lens as the imaging lens 5, which enables further cost reduction. Further, when a mirror is disposed, it is necessary to ensure a space of a reflecting surface, which makes it difficult to achieve downsizing.

(Lens Configuration)

A specific lens configuration of the imaging lens 5 will be described later in each example. Hereinbelow, first, a basic lens configuration of the imaging lens 5 will be simply described. The lens L1 which is disposed on the most observation subject side of the imaging lens 5 preferably has negative refractive power. Disposing the lens L1 having negative refractive power on the most observation subject side makes it easy to avoid upsizing while achieving a wider angle of the imaging lens 5.

A lens L2 (a second lens L2 in Examples 1, 2 and a third lens L3 in Example 3) having positive refractive power is preferably disposed on the image side of the lens L1. Disposing the lens having positive refractive power on the image side of the lens having negative refractive power enables downsizing of the lens L1 in the radial direction. Further, the lens L2 is more preferably disposed adjacent to the image side of the lens L1. Disposing the lens L1 having negative refractive power and the lens L2 having positive refractive power in this order from the observation subject side enables the imaging lens 5 to have a wider angle while downsizing the lens L1 in the radial direction.

Further, the imaging lens 5 preferably includes at least one lens N having negative refractive power on the image side relative to the lens L1 for correction of an image plane performance. It is necessary to reduce the Petzval sum for correction to improve the image plane performance in the imaging lens 5. Disposing at least one lens N having positive refractive power makes it easy to reduce the Petzval sum in the entire imaging lens 5. More specifically, when the lens L1 having negative refractive power is disposed on the most observation subject side, aberrations cancel each other out by disposing the lens N having negative refractive power on the image side relative to the lens L1, which is effective for correction of distortion aberration or field curvature.

Further, at least one of the lenses constituting the imagine lens 5 is preferably a lens made of resin (so-called plastic lens, hereinbelow, also referred to as a resin lens) for cost reduction. In addition, the imaging lens 5 preferably includes a combination of a resin lens having positive refractive power and a resin lens having negative refractive power. Further, this combination is preferably increased to one set, two sets, and three sets. Accordingly, various aberrations caused by the resin lenses having a temperature characteristic different from that of a lens made of glass can be effectively cancelled each other out. Thus, it is possible to prevent reduction in the performance while achieving cost reduction. Further, at least one face of the resin lens preferably has an aspherical surface having a shape that weakens the refractive power of a paraxial curvature in view of higher performance.

[Image Sensor]

The image sensor 6 is disposed on the image side of the imaging lens 5, and converts an observation subject image (optical image) formed by the imaging lens 5 to an electric signal (image data).

The image sensor 6 is not particularly limited to any sensor. For example, a solid-state image sensor such as a charge coupled device (CCD) sensor or a complementary metal oxide semiconductor (COMS) sensor can be used as the image sensor 6. The resolution and size of the solid-state image sensor are also not particularly limited to any resolution and size. However, the resolution of the solid-state image sensor is preferably equal to or higher than the resolution of full-high vision, more preferably equal to or higher than the resolution of 4K, and further more preferably equal to or higher than the resolution of 8K.

With an increase in pixel count of the image sensor 6, an effective imaging range of the image sensor 6 expands, which also upsizes the imaging lens 5. Thus, in order to achieve both downsizing and higher pixel count in the entire observation imaging apparatus 1, it is necessary to employ the image sensor 6 having an optimal size. The size of the image sensor 6 will be described later.

Although the present embodiment describes, as an example, a configuration in which the image sensor 6 includes one image sensor, the image sensor 6 is not limited thereto. For example, when a plurality of image sensors are disposed with their imaging surfaces (the surfaces on which an observation subject image is formed by the imaging lens 5) not overlapping each other, and the optical path of the imaging lens 5 is spilt by a split prism or the like to condense light on the imaging surface of each of the image sensors, the image sensors as a whole have a function equivalent to one large image sensor. When a plurality of image sensors are used in this manner, the imaging surface of the image sensor 6 means the imaging surface of one large image sensor which is regarded as being equivalent to the plurality of image sensors. A pixel pitch of the image sensor 6 (described later) indicates the distance between the centers of pixels adjacent to each other on the imaging surface, and indicates a displacement amount of pixels when a plurality of image sensors are disposed with their pixels displaced.

[Image Processing Unit]

The observation imaging apparatus 1 according to the present embodiment is provided with an image processing unit 7 which electrically processes image data generated in the image sensor 6. The image processing unit 7 electrically processes image data input thereto to generate corrected image data, and outputs the generated corrected image data.

The imaging lens 5 is preferably an optical system having a small size and a wide angle. However, in such an optical system, an optical image formed on the image sensor 6 is prone to become distorted. Thus, the image processing unit 7 which electrically processes distortion of an observation subject image represented by image data generated by the image sensor 6 enables the generation of a corrected observation subject image having less distortion. In the present embodiment, the image processing unit 7 is provided with a recording unit and a processing unit (e.g., a CPU) (both not illustrated). Correction data for correcting distortion of an observation subject image represented by image data is previously recorded on the recording medium. The processing unit corrects the image data on the basis of the correction data read from the recording unit.

(Correction of Observation Subject Image)

The image processing unit 7 preferably electrically processes data on distortion aberration in the image data representing the observation subject image. Accordingly, it is possible to generate corrected image data having a small distortion aberration in the image processing unit 7 while achieving a wider angle of the imaging lens 5 by disposing the lens L1 having negative refractive power on the most observation subject side of the imaging lens 5. Thus, a user can refer to an image having a wide angle of view and a small distortion aberration by referring to the corrected observation subject image represented by the corrected image data, the corrected observation subject image being displayed on a display device or the like. Further, the image processing unit 7 may electrically process data on chromatic aberration of magnification in the image data. When the data on chromatic aberration of magnification can be electrically processed, a corrected observation subject image having a small chromatic aberration can be obtained. This makes it possible to reduce the number of lenses constituting the imaging lens 5, which further facilitates downsizing of the entire observation imaging apparatus 1.

Further, the imaging lens 5 may be disposed rotatably about a normal line A (described later) (that is, with respect to the length direction of the insertion unit 2). At this time, in the case of a configuration in which the insertion unit 2 does not rotate, and only the imaging lens 5 is rotatable, the window 4 is preferably formed over the entire circumference of the tip part 3. Further, in the case of a configuration in which the imaging lens 5 is rotatable integrally with the tip part 3, the image processing unit 7 may electrically process and combine a plurality of image data items corresponding to a plurality of observation subject images which is captured while rotating the tip part 3 to generate combined image data representing one combined image of a wide area.

Accordingly, it is possible to obtain an observation subject image in which an image of a wide area is captured in a pseudo manner. Thus, it is possible to achieve a wider angle not by the imaging lens 5 only, but by both the imaging lens 5 and the image processing unit 7. This eliminates the necessity of demanding higher performance of the imaging lens 5 more than necessary. Thus, it becomes possible to reduce the number of lenses constituting the imaging lens 5, thereby downsizing the observation imaging apparatus 1.

[Tilted Disposition of Imaging Lens]

Figure 2B:
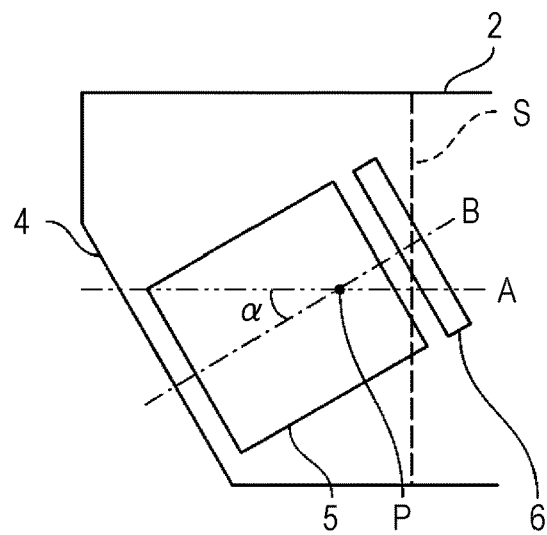
Figure 2C:
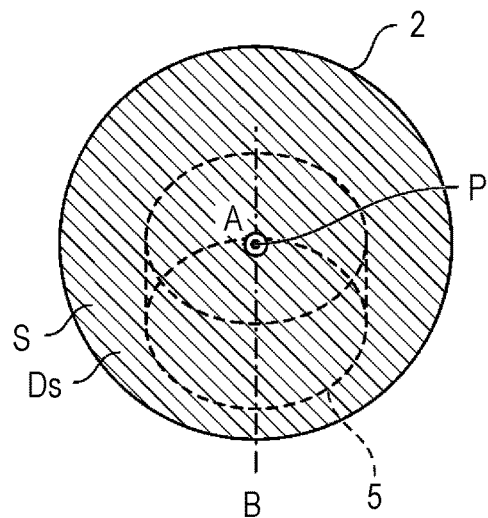

Next, the disposition of the imaging lens 5 in the insertion unit 2 (more specifically, the tip part 3 of the insertion unit 2) will be described with reference to FIGS. 2A to 2C. FIGS. 2A to 2C are diagrams simply illustrating the disposition of the imaging lens 5 inside the insertion unit 2. FIG. 2A is a perspective view of the observation imaging apparatus 1, FIG. 2B is a sectional view of the observation imaging apparatus 1 in the insertion direction, and FIG. 2C is a sectional view of the insertion unit 2 on a cross section S. For simplifying the description of the disposed position of the imaging lens 5 disposed inside the observation imaging apparatus 1, the imaging lens 5 is indicated by a broken line in FIGS. 2A and 2C.

As illustrated in FIGS. 2A to 2C, in the observation imaging apparatus 1, in order to capture an image inside a narrow space, the imaging lens 5 is disposed in a tilted state with respect to the insertion direction of the insertion unit 2 in the tip part 3 of the insertion unit 2. In other words, when a normal line passing through the center of gravity of the cross section S of the insertion unit 2, the cross section S passing through the center of the image sensor 6 (the center of the effective imaging range of the image sensor 6) and being perpendicular to the insertion direction of the insertion unit 2, is defined as the normal line A, the imaging lens 5 is fixed to the insertion unit 2 in such a manner that an axial principal ray B of the observation subject side surface of the lens L1 is tilted (having an angle) with respect to the normal line A. Hereinbelow, the direction along the axial principal ray B of the observation subject side surface of the lens L1 is also merely referred to as the imaging direction of the imaging lens 5.

When the imaging lens 5 is disposed with the imaging direction of the imaging lens 5 oblique with respect to the insertion direction of the insertion unit 2 in this manner, the observation imaging apparatus 1 can effectively capture an image in an oblique direction with respect to the insertion direction of the insertion unit 2.

Further, when a point on the axial principal ray B at which the distance between the normal line A and the axial principal ray B is smallest (in the present embodiment, an intersection point of the normal line A and the axial principal ray B) is defined as a point P, the point P is preferably present on the image side relative to the most observation subject side surface of the imaging lens 5 and on the observation subject side relative to the image sensor 6. In order to achieve a higher resolution of the imaging lens 5 while downsizing the insertion unit 2, it is necessary to increase the disposition efficiency of the imaging lens 5 with respect to the size of the insertion unit 2. The above configuration enables the imaging lens 5 to be efficiently disposed while reducing a gap (a space in the insertion unit 2 where the imaging lens 5 is not disposed) with respect to the size of the insertion unit 2.

Further, with an increase in pixel count of the image sensor 6 (expansion of the effective imaging range), the imaging lens 5 is also upsized. Thus, in order to achieve both downsizing and higher pixel count, the imaging lens 5 is preferably disposed with an optimal tilt amount. The optimal tilt amount of the imaging lens 5 should be determined taking into consideration the size of the imaging lens 5 and the size of the insertion unit 2.

As illustrated in FIG. 2B, when α denotes an angle between the normal line A and the axial principal ray B which intersect each other at the point P, the angle α represents a tilt of the imaging lens 5 in the imaging direction with respect to the insertion direction of the insertion unit 2. Details of the angle α (that is, the tilt of the imaging lens 5 in the imaging direction) will be described later together with a conditional expression.

In the present embodiment, the image sensor 6 and the effective imaging range thereof have a substantially rectangular shape. At this time, when the longitudinal direction of the rectangle is parallel to a plane including the angle α between the normal line A and the axial principal ray B and the axial principal ray B (that is, the tilt direction of the imaging lens 5 is the same as the longitudinal direction of the image sensor 6), the angle by which the imaging lens 5 can be tilted is reduced. Thus, the image sensor 6 is preferably disposed with the plane including the angle α and the axial principal ray B substantially parallel to the lateral direction of the image sensor 6 (with the plane substantially perpendicular to the longitudinal direction). Accordingly, it is possible to increase the tilt angle of the imaging lens 5.

[Other Configurations of Observation Imaging Apparatus]

The observation imaging apparatus 1 according to the present embodiment may be provided with an illumination unit 8 in the tip 3 of the insertion unit 2. Accordingly, a required quantity of light can be secured from the illumination unit 8 even when a quantity of light required for imaging cannot be obtained from the surroundings due to insertion into a narrow space. Further, in the illumination unit 8, a principal illumination direction (an orientational axis illuminated by the illumination unit 8) is preferably substantially parallel to the axial principal ray B of the observation subject side surface of the lens L1 included in the imaging lens 5 (that is, the illumination direction and the imaging direction are the same direction) in view of illumination efficiency.

Further, the observation imaging apparatus 1 according to the present embodiment is provided with a display device 9. The display device 9 is not particularly limited to any display device, and may be, for example, a liquid crystal television, an organic EL television, or a monitor of a personal computer. Accordingly, a lot of people can observe an observation subject image at the same time by displaying image data (or corrected image data or combined image data) on the observation subject image acquired by the observation imaging apparatus 1.

Although, in the present embodiment, the observation imaging apparatus 1 is provided with the display device 9 as an example, the present invention is not limited thereto. For example, the display device 9 may be prepared separately from the observation imaging apparatus 1, and the observation imaging apparatus 1 may be capable of outputting image data to the display device 9. Further, a method for connecting the observation imaging apparatus 1 and the display device 9 is not limited to wired connection. For example, the observation imaging apparatus 1 and the display device 9 may be wirelessly connected via Bluetooth (registered trademark) or Wi-Fi. In this case, for example, a portable terminal, such as a smartphone or a tablet terminal, can also be employed as the display device 9.

Further, the observation imaging apparatus 1 according to the present embodiment may include an operation unit which performs an operation (treatment) on an observation subject in the tip part 3 of the insertion unit 2.

Further, in the observation imaging apparatus 1 according to the present embodiment, the tip part 3 of the insertion unit 2 may be rotatable together with the imaging lens 5 with respect to the insertion direction as described above. In this case, the imaging lens 5 and the image sensor 6 are preferably disposed with their optical axes directed in the same direction as illustrated in FIG. 1. The image sensor 6 and the image processing unit 7 are preferably connected in a wired manner using, for example, a soft wire or wirelessly connected. This facilitates the rotation of the tip part 3.

Further, the observation imaging apparatus 1 according to the present embodiment may be configured in such has manner that the tip part 3 is removable from the insertion unit 2. For example, a mount part, which can be electrically connected so that image data output from the image sensor 6 can be transmitted to the image processing unit 7, may be disposed on one end opposite to the side at which the imaging lens 5 is disposed in the tip part 3 in which the imaging lens 5 and the image sensor 6 are disposed, and the tip part 3 may be connectable to the insertion unit 2 through the mount part of the insertion unit 2. Further, when the image sensor 6 and the image processing unit 7 are wirelessly connected, the tip part 3 and the insertion unit 2 may be merely mechanically connected.

With this configuration, the tip part 3 can be replaced every time the tip part 3 gets dirty by using the observation imaging apparatus 1 or every time the observation imaging apparatus 1 is used. Thus, it is possible to use the observation imaging apparatus 1 in a clean state without replacing the entire observation imaging apparatus 1. When the observation imaging apparatus 1 is used as an endoscope which observes the inside of the human body, it is necessary to perform sterilization (e.g., sterilization by boiling at high temperature) of the tip part 3 every time the observation imaging apparatus 1 is used once. However, when the tip part 3 is replaceable, it is not necessary to repeatedly use the observation imaging apparatus 1 having a deteriorated imaging performance due to sterilization and more hygienically use the observation imaging apparatus 1.

[Adjustment of Imaging Lens]

The observation imaging apparatus 1 according to the present embodiment is preferably capable of reducing an error amount caused by a manufacturing error by adjusting air spacing between lenses inside the imaging lens 5. For example, as a pixel pitch PIT of the image sensor 6 becomes finer and a permissible circuit of confusion becomes smaller, an aberration allowable amount required of the observation imaging apparatus 1 becomes smaller. Thus, an aberration caused by a manufacturing error that occurs in processing of a lens, processing of a lens frame, and an assembling process increases. Thus, in order to achieve higher performance, it is necessary to reduce the error amount caused by the manufacturing error by adjusting the air spacing between lenses of the imaging lens 5.

Examples of the error amount caused by the manufacturing error include back, spherical aberration, field curvature, and chromatic aberration. A method for adjusting the air spacing between lenses is not particularly limited to any method. A change location, the number of changes, a change method, and the number of times of change can be appropriately selected.

Further, the observation imaging apparatus 1 is preferably also capable of reducing a decentering error amount caused by the manufacturing error by decentering at least one lens included in the imaging lens 5. The decentering error amount caused by the manufacturing error indicates axial coma, one-side blur, an image height error, color shift, or the like.

Further, decentering a lens indicates decentering the lens in the direction perpendicular to the optical axis or tilting the lens with respect to the optical axis to adjust the position of the lens. A change location, the number of changes, a change method, the number of times of change, and a rotation center thereof can be determined in any manner. Further, the number of lenses used in the decentering adjustment may be one or more, and can be determined in any manner.

[Description of Conditional Expressions]

The observation imaging apparatus 1 according to the present invention preferably satisfies any one or more of the following conditional expressions in addition to the above configuration.

(Conditional Expression (1))

The observation imaging apparatus 1 preferably satisfies the following conditional expression:

$$0.10 < Dm/Ds < 0.80 \tag{1}$$

where

Dm is the area of the effective imaging range of the image sensor 6, and

Ds is the area of the cross section S.

The conditional expression (1) is an expression for defining the ratio between the area of the effective imaging range of the image sensor 6 and the area of the cross section S of the insertion unit 2. When the conditional expression (1) is satisfied, it is possible to effectively dispose the image sensor 6 whose effective imaging range has a large area and select the image sensor 6 having an appropriate size with respect to the size of the insertion unit 2.

When the value of the conditional expression (1) exceeds the upper limit, the effective imaging range of the image sensor 6 becomes too large with respect to the area of the cross section S, which makes it difficult to dispose the image sensor 6 in the insertion unit 2. On the other hand, when the value of the conditional expression (1) falls below the lower limit, the effective imaging range of the image sensor 6 becomes too small with respect to the area of the cross section S, which makes it difficult to obtain a required resolution. Thus, the value falling below the lower limit is not preferred in view of high performance. Further, since the area of the cross section S becomes too large with respect to the effective imaging range of the image sensor 6, the value falling below the lower limit is not preferred in view of downsizing.

The lower limit of the conditional expression (1) is preferably 0.15, more preferably 0.20, further more preferably 0.25, still further more preferably 0.30, and still further more preferably 0.35. Further, the upper limit of the conditional expression (1) is preferably 0.75, more preferably 0.70, further more preferably 0.65, still further more preferably 0.60, and still further more preferably 0.55.

(Conditional Expression (2))

The observation imaging apparatus 1 preferably satisfies the following conditional expression:

$$-50.00 < fL1/f < -0.01 \tag{2}$$

where fL1 is the focal length of the lens L1, and f is the focal length of the imaging lens 5.

The conditional expression (2) is an expression for defining the ratio between the focal length of the lens L1 which is disposed on the most observation subject side of the imaging lens 5 and the focal length of the imaging lens 5. When the conditional expression (2) is satisfied, it is possible to achieve a wider angle while avoiding upsizing of the lens L1 in the radial direction.

When the value of the conditional expression (2) exceeds the upper limit, the focal length of the lens L1 becomes too short with respect to the focal length of the imaging lens 5, which results in the occurrence of distortion aberration, field curvature, or coma aberration. Thus, the value exceeding the upper limit is not preferred in view of higher performance. When the value of the conditional expression (2) falls below the lower limit, the focal length of the lens L1 becomes too long with respect to the focal length of the imaging lens 5, which makes it difficult to set an entrance pupil position on the observation subject side of the imaging lens 5 and thus causes upsizing of the lens L1 in the radial direction. Thus, the value falling below the lower limit is not preferred in view of downsizing.

The lower limit of the conditional expression (2) is more preferably −20.00, further more preferably −10.00, still further more preferably −7.00, still further more preferably −5.00, and still further more preferably −3.00. The upper limit of the conditional expression (2) is more preferably −0.05, further more preferably −0.10, still further more preferably −0.15, still further more preferably −0.20, and still further more preferably −0.30.

(Conditional Expression (3))

The observation imaging apparatus 1 preferably satisfies the following conditional expression (3):

$$0.02 < fL2/|fL1| < 20.00 \tag{3}$$

where fL1 is the focal length of the lens L1, and fL2 is the focal length of the lens L2 which is disposed on the image side of the lens L1 and has positive refractive power.

The conditional expression (3) is an expression for defining the ratio between the focal length of the lens L1 which is disposed on the most observation subject side of the imaging lens 5 and the focal length of the lens L2 which is disposed on the image side of the lens L1 and has positive refractive power. When the lens L1 having negative refractive power is disposed on the most observation subject side and the lens L2 having positive refractive power is disposed adjacent to the image side of the lens L1, and the conditional expression (3) is satisfied, it is possible to achieve both a wider angle of the imaging lens 5 and downsizing in the total length.

When the value of the conditional expression (3) exceeds the upper limit, the focal length of the lens L2 becomes too long with respect to the absolute value of the focal length of the lens L1, which weakens a convergence action in the lens L2 and makes it difficult to shorten the total length. Thus, the value exceeding the upper limit is not preferred in view of downsizing. When the value of the conditional expression (3) falls below the lower limit, the focal length of the lens L2 becomes too short with respect to the absolute value of the focal length of the lens L1, which results in the occurrence of spherical aberration, field curvature, or coma aberration. Thus, the value falling below the lower limit is not preferred in view of higher performance.

The lower limit of the conditional expression (3) is more preferably 0.08, further more preferably 0.15, still further more preferably 0.25, still further more preferably 0.35, and still further more preferably 0.45. The upper limit of the conditional expression (3) is more preferably 5.00, further more preferably 3.50, still further more preferably 2.50, still further more preferably 2.00, and still further more preferably 1.50.

(Conditional Expression (4))

The observation imaging apparatus 1 preferably satisfies the following conditional expression:

$$1.500 < NdN < 2.200 \tag{4}$$

where

NdN is the refractive index of the lens N at the d-line.

The conditional expression (4) is an expression for defining the refractive index of at least one lens N which is disposed on the image side relative to the lens L1 in the imaging lens 5 and has negative refractive power. When the conditional expression (4) is satisfied, it is possible to satisfactorily correct the image plane performance in the imaging lens 5.

When the value of the conditional expression (4) exceeds the upper limit, the refractive index of the lens N becomes too high, which results in high cost of the material. Thus, the value exceeding the upper limit is not preferred in view of cost reduction. Further, when the value of the conditional expression (4) falls below the lower limit, it becomes difficult to correct the Petzval sum. Thus, the value falling below the lower limit is not preferred in view of higher performance.

The lower limit of the conditional expression (4) is more preferably 1.510, further more preferably 1.520, and still further more preferably 1.530. The upper limit of the conditional expression (4) is more preferably 2.060, further more preferably 2.010, still further more preferably 1.960, still further more preferably 1.890, and still further more preferably 1.850.

(Conditional Expression (5))

The observation imaging apparatus 1 preferably satisfies the following conditional expression:

$$0.2 < OAL/YY < 10.0 \quad (5)$$

where

OAL is the distance from the observation subject side surface of the lens L1 to the imaging plane, and YY is the effective diagonal length of the image sensor 6.

The conditional expression (5) is an expression for defining the ratio between the distance from the observation subject side surface of the lens L1 to the imaging plane and the effective diagonal length of the image sensor 6. With an increase in pixel count, the effective imaging range of the image sensor 6 tends to expand. However, in order to downsize the insertion unit 2, it is necessary to select the image sensor 6 having an appropriate size with respect to the size of the imaging lens 5. When the conditional expression (5) is satisfied, it is possible to dispose the image sensor 6 having an appropriate size with respect to the size of the imaging lens 5 to downsize the insertion unit 2.

When the value of the conditional expression (5) exceeds the upper limit, the total length of the imaging lens 5 becomes too long with respect to the effective diagonal length of the image sensor 6, which makes it difficult to dispose the imaging lens 5 in a tilted state with respect to the insertion unit 2. Thus, the value exceeding the upper limit is not preferred. When the value of the conditional expression (5) falls below the lower limit, the total length of the imaging lens 5 becomes too short with respect to the effective diagonal length of the image sensor 6, which makes it difficult to achieve the imaging lens 5 having a small aberration amount corresponding to high resolution. Thus the value falling below the lower limit is not preferred.

The lower limit of the conditional expression (5) is more preferably 0.3, further more preferably 0.4, still further more preferably 0.5, still further more preferably 0.6, and sill further more preferably 0.7. The upper limit of the conditional expression (5) is more preferably 8.0, furthermore preferably 6.0, still further more preferably 4.0, still further more preferably 3.0, and sill further more preferably 2.0.

(Conditional Expression (6))

The observation imaging apparatus 1 preferably satisfies the following conditional expression:

$$0.30 < |fLP|/f < 10.00 \quad (6)$$

where fLP is the focal length of the lens made of resin, and f is the focal length of the imaging lens.

The conditional expression (6) is an expression for defining the ratio between the focal length of the resin lens and the focal length of the imaging lens 5. When the conditional expression (6) is satisfied, it is possible to achieve an appropriate refractive power of the resin lens to achieve higher performance while reducing cost. Further, this configuration is also effective in downsizing of the imaging lens 5 in the total length direction. When the imaging lens 5 includes a plurality of resin lenses, at least one of the resin lenses may satisfy the conditional expression (6). More preferably, when all of the resin lenses satisfy the conditional expression (6), it is possible to achieve further higher performance.

The conditional expression (6) is a condition for optimizing the refractive power of the lens made of resin. When the value of the conditional expression (6) exceeds the upper limit, the focal length of the resin lens becomes too long with respect to the focal length of the imaging lens 5. Thus, an aberration correction capability of the resin lens becomes insufficient. In order to make up for the shortage in aberration correction, it is necessary to increase the number of lenses. In this case, cost reduction and downsizing in the total length cannot be achieved. Thus, the value exceeding the upper limit is not preferred. When the value of the conditional expression (6) falls below the lower limit, the focal length of the resin lens becomes too short with respect to the focal length of the imaging lens 5, which results in an excessive aberration correction amount of the resin lens and makes it difficult to achieve higher performance. Thus, the value falling below the lower limit is not preferred.

The lower limit of the conditional expression (6) is more preferably 0.40, further more preferably 0.45, still further more preferably 0.50, still further more preferably 0.55, and still further more preferably 0.60. The upper limit of the conditional expression is more preferably 9.00, further more preferably 8.00, still further more preferably 7.00, still further more preferably 6.00, and still further more preferably 5.00.

(Conditional Expression (7))

The observation imaging apparatus 1 preferably satisfies the following conditional expression:

$$20.0 < YY/PIT/Fno < 800.0 \quad (7)$$

where

YY is the effective diagonal length of the image sensor 6,

PIT is the pixel pitch of the image sensor 6, and

Fno is the F number of the imaging lens 5.

The conditional expression (7) is an expression for defining the size and the pixel pitch of the image sensor 6, and the F number of the imaging lens 5. When the conditional expression (7) is satisfied, it is possible to achieve an appropriate relationship between the number of pixels (YY/PIT) of the image sensor 6 and the F number of the imaging lens 5 to satisfactorily perform aberration correction with a small number of lenses. Thus, it is possible to obtain an observation optical system (the optical system including the imaging lens 5 and the image sensor 6) having a small size and a high resolution.

When the value of the conditional expression (7) exceeds the upper limit, that is, when the F number of the imaging lens 5 becomes too small with respect to the number of pixels of the image sensor 6, it becomes difficult to satisfactorily perform aberration correction with a small number of lenses. In order to obtain the imaging lens having a high resolution, it is difficult to downsize the imaging lens 5.

Thus, the value exceeding the upper limit is not preferred. On the other hand, the value of the conditional expression (7) falls below the lower limit, that is, when the F number of the imaging lens 5 becomes too large with respect to the number of pixels of the image sensor 6, the resolution performance of a high-frequency component becomes low due to diffraction limit. Thus, the value falling below the lower limit is not preferred.

The lower limit of the conditional expression (7) is more preferably 22.0, further more preferably 25.0, still further more preferably 30.0, still further more preferably 35.0, and still further more preferably 40.0. The upper limit of the conditional expression (7) is more preferably 750.0, further more preferably 700.0, still further more preferably 650.0, still further more preferably 600.0, and still further more preferably 550.0.

(Conditional Expression (8))

The observation imaging apparatus 1 preferably satisfies the following conditional expression:

$$2.0 < L/OAL \tag{8}$$

where

L is the length of the insertion unit 2 in the insertion direction, and

OAL is the distance from the lens surface on the most observation subject side of the imaging lens 5 to the imaging plane.

The conditional expression (8) is an expression for defining the ratio between the total length of the imaging lens 5 and the length of the insertion unit 2 in the insertion direction. In the observation imaging apparatus 1, in order to capture an image of a narrow space or the like, it is required that the length of the insertion unit 2 in the insertion direction be long to some extent with respect to the total length of the imaging lens 5. When the conditional expression (8) is satisfied, a sufficient length of the insertion unit 2 in the insertion direction can be secured with respect to the total length of the imaging lens 5. Thus, a shape suitable for capturing an image of a narrow space or the like can be obtained.

When the value of the conditional expression (8) falls below the lower limit, the length of the insertion unit 2 in the insertion direction becomes too short with respect to the total length of the imaging lens 5, which limits imaging of the narrow space in the depth direction. Thus, the value falling below the lower limit is not preferred. Further, the upper limit of the conditional expression (8) is not limited to any value. However, a too-long insertion unit is also inconvenient when used. Thus, the upper limit is preferably 500.0 in view of downsizing of the observation imaging apparatus 1.

The lower limit of the conditional expression (8) is more preferably 2.5, further more preferably 3.0, still further more preferably 3.5, still further more preferably 4.0, and still further more preferably 4.5. The upper limit of the conditional expression (8) is more preferably 450.0, further more preferably 400.0, still further more preferably 350.0, still further more preferably 300.0, and still further more preferably 250.0.

(Conditional Expression (9))

The observation imaging apparatus 1 preferably satisfies the following conditional expression:

$$0.00 \leq \tan(|\beta| - |\alpha|) < 2.00 \tag{9}$$

where $\alpha$ is the angle between the normal line A and the axial principal ray B, and $\beta$ is the half angle of view of the most off-axial principal ray of the imaging lens 5.

The conditional expression (9) is an expression for defining the relationship between the angle $\alpha$ between the normal line A and the axial principal ray B and the half angle of view $\beta$ of the most off-axial principal ray of the imaging lens 5. The imaging lens 5 is disposed in a titled state with respect to the normal line A of the cross section S of the insertion unit 2 as described above. Thus, $|\alpha|$ has a value larger than zero. When the conditional expression (9) is satisfied, it is possible to achieve an appropriate relationship between the tilt of the imaging lens 5 and the half angle of view of the most off-axial principal ray of the imaging lens 5 to ensure a wide imaging range with respect to the insertion direction without using a super wide angle lens while preventing a dead angle of the imaging lens 5 from being generated in the insertion direction of the insertion unit 2.

Since the conditional expression (9) has a value of zero or higher, the imaging lens 5 is disposed so that the tilt $\alpha$ is smaller than the half angle of view $\beta$ of the most off-axial principal ray. When the value of the conditional expression (9) falls below the lower limit, that is, the angle $\alpha$ has a large value, there is a dead angle in the direction of the normal line A in the relationship $|\beta| - |\alpha|$ with the half angle of view $\beta$. Thus, the value falling below the lower limit is not preferred. When the value of the conditional expression (9) exceeds the upper limit, an image in a wide range with respect to the axis in the insertion direction cannot be captured. Thus, the value exceeding the upper limit is not preferred.

The upper limit of the conditional expression (9) is more preferably 1.80, further more preferably 1.60, still further more preferably 1.40, still further more preferably 1.20, and still further more preferably 1.00.

(Conditional Expression (10))

The observation imaging apparatus 1 preferably satisfies the following conditional expression:

$$0.01 < (OAL \times \sin|\alpha| + YY \times \cos|\alpha|)/DI < 5.00 \tag{10}$$

where

OAL is the distance from the most observation subject side lens surface of the imaging lens to the imaging plane, $\alpha$ is the angle between the normal line A and the axial principal ray B, YY is the effective diagonal length of the image sensor, and DI is the diameter of a circumcircle of the cross section S.

The conditional expression (10) is an expression for defining the condition for efficiently disposing the imaging lens 5 in the insertion unit 2. With an increase in pixel count, the effective imaging range of the image sensor 6 expands. However, in order to downsize the insertion unit 2, it is necessary to select the image sensor 6 having an appropriate size with respect to the size of the imaging lens 5 which is disposed inside the insertion unit 2 and optimize the tilt amount of the imaging lens 5.

Figure 3:
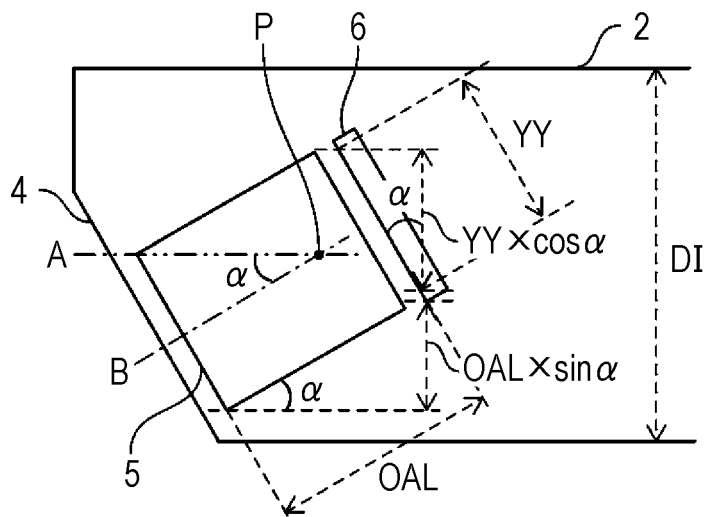
FIG. 3 is a diagram schematically illustrating the angular relationship when the imaging lens is disposed in a tilted state with respect to the insertion unit in the observation imaging apparatus according to the embodiment of the present invention.

FIG. 3 schematically illustrates the angular relationship when the imaging lens 5 is disposed in a titled state with respect to the insertion unit 2. Further, YY denotes the effective diagonal length of the image sensor 6 as described above. In the example illustrated in FIG. 3, the image sensor 6 is disposed with one of diagonal lines thereof parallel to a plane including the angle $\alpha$.

As illustrated in FIG. 3, the disposition height of the imaging lens 5 in the diameter direction of the insertion unit 2 can be represented by the length sum of $OAL \times \sin|\alpha|$ and $YY \times \cos|\alpha|$ in a pseudo manner. That is, the conditional expression (10) defines the proportion of the imaging lens 5 with respect to the diameter direction of the insertion unit 2. Thus, when the conditional expression (10) is satisfied, it is possible to improve the disposition efficiency when the imaging lens 5 is disposed in a tilted state with respect to the insertion direction to achieve both downsizing of the insertion unit 2 and improvement in the disposition efficiency.

When the value of the conditional expression (10) falls below the lower limit, the disposition efficiency of the imaging lens 5 with respect to the size of the insertion unit 2 is reduced, which results in upsizing of the insertion unit 2. Thus, the value falling below the lower limit is not preferred. When the value of the conditional expression (10) exceeds the upper limit, it is physically difficult to dispose the imaging lens 5 with respect to the size of the insertion unit 2. Thus, the value exceeding the upper limit is not preferred.

The lower limit of the conditional expression (10) is more preferably 0.10, further more preferably 0.15, still further more preferably 0.20, still further more preferably 0.25, and still further more preferably 0.30. The upper limit of the conditional expression (10) is more preferably 4.00, further more preferably 3.00, still further more preferably 2.00, still further more preferably 1.00, and still further more preferably 0.80.

Although FIG. 3 illustrates, as an example, the configuration in which the image sensor 6 is disposed with one diagonal line parallel to the plane including the angle α, the present invention is not limited thereto. For example, the image sensor 6 may be disposed with the lateral direction thereof parallel to the plane including the angle α. In this case, since the lateral direction of the image sensor 6 can be located along the plane including the angle α, it is possible to most efficiently dispose the imagine lens 5 inside the insertion unit 2.

(Conditional Expression (11))

The observation imaging apparatus 1 preferably satisfies the following conditional expression:

$$0.00 \leq \tan|\gamma| < 0.60 \qquad (11)$$

where

γ is the angle between a plane formed by the angle α between the normal line A and the axial principal ray B and the axial principal ray B and the lateral direction of the effective imaging range of the image sensor 6.

The conditional expression (11) is a conditional expression for defining the relationship between the direction in which the imaging lens 5 is tiled and the disposition of the image sensor 6.

Figure 4A:
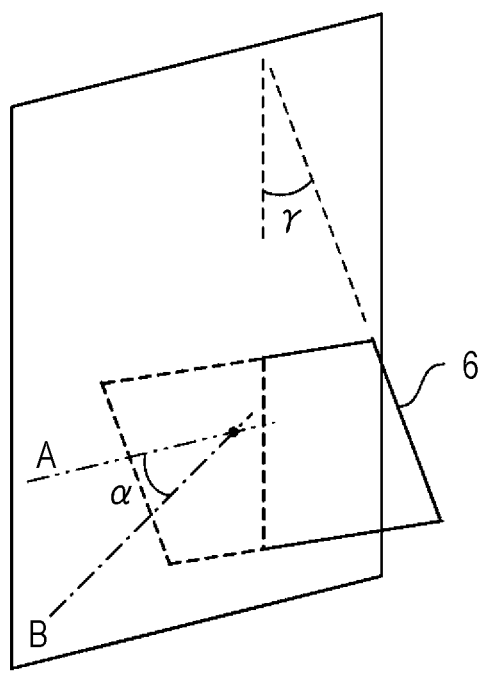
FIGS. 4A and 4B are diagrams schematically illustrating the disposition relationship between a plane formed by an angle α between a normal line A and an axial principal ray B and the axial principal ray B and an image sensor.
Figure 4B:
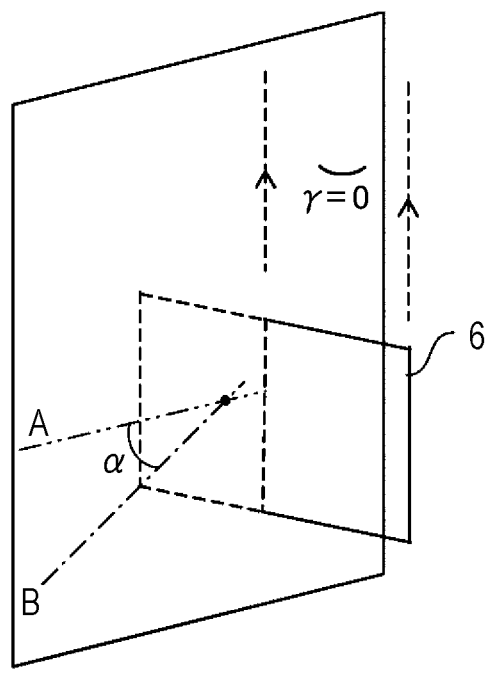

FIGS. 4A and 4B schematically illustrate the disposition relationship between the plane formed by the angle α between the normal line A and the axial principal ray B and the axial principal ray B (the plane including the angle α between the normal line A and the axial principal ray B) and the image sensor 6. Further, the plane formed by the angle α between the normal line A and the axial principal ray B and the axial principal ray B represents a section of the insertion unit 2 in the tilt direction of the imaging lens 5.

As illustrated in FIG. 4A, when the image sensor 6 is disposed in a tilted state with respect to the plane including the angle α between the normal line A and the axial principal ray B, the angle between the plane and the lateral direction of the effective imaging range is γ. As illustrated in FIG. 4B, when the image sensor 6 is disposed with the plane parallel to the lateral direction, the angle γ=0.

When the conditional expression (11) is satisfied, the tilt direction of the imaging lens 5 and the lateral direction of the image sensor 6 can be made substantially the same direction, and it is possible to downsize the insertion unit 2 and, by extension, downsize the observation imaging apparatus 1. When the value of the conditional expression (11) exceeds the upper limit, the tilt direction of the imaging lens 5 and the lateral direction of the image sensor 6 are not the same direction (the angle between the tilt direction of the imaging lens 5 and the lateral direction of the image sensor 6 becomes large), which upsizes the insertion unit 2. Thus, the value exceeding the upper limit is not preferred.

The upper limit of the conditional expression (11) is more preferably 0.57 (γ=approximately 30°), further more preferably 0.50 (γ=approximately 26°), still further more preferably 0.45 (γ=approximately 24°), still further more preferably 0.40 (γ=approximately 22°), still further more preferably 0.35 (γ=approximately 19°), still further more preferably 0.25 (γ=approximately 15°), still further more preferably 0.17 (γ=approximately 10°), and still further more preferably 0.10 (γ=approximately 5°).

Second Embodiment

Figure 5A:
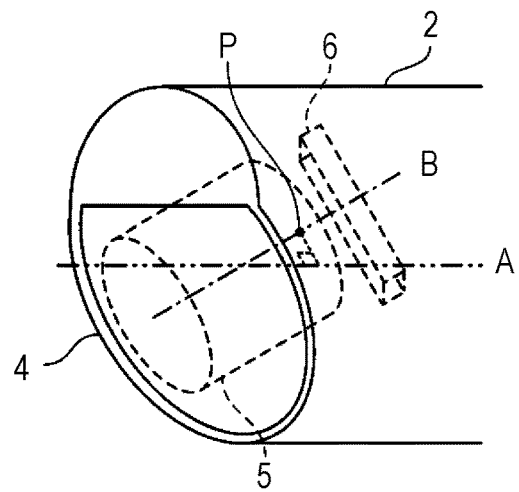
FIGS. 5A to 5C are diagrams illustrating an example of an observation imaging apparatus according to another embodiment of the present invention.
Figure 5B:
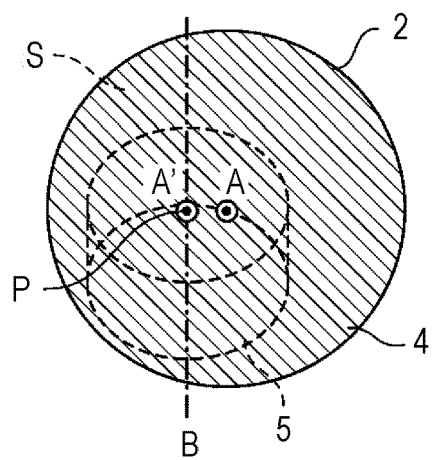
Figure 5C:
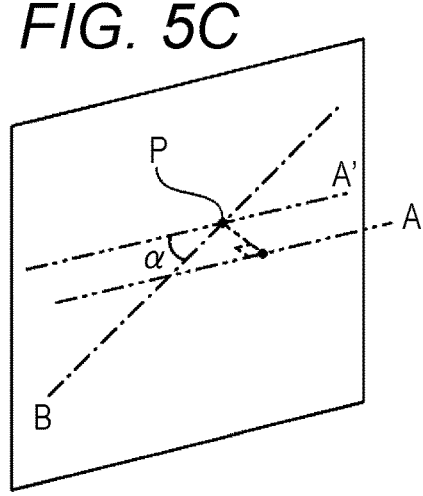

Next, an observation imaging apparatus 11 according to another embodiment of the present invention will be described with reference to FIGS. 5A to 5C. FIGS. 5A to 5C are diagrams illustrating an example of the observation imaging apparatus 11 according to another embodiment of the present invention. FIG. 5A is a perspective view of the observation imaging apparatus 11. FIG. 5B is a sectional view of an insertion unit 12 on a cross section S. FIG. 5C is a diagram schematically illustrating an angle α. For simplifying the description of the disposed position of an imaging lens 5 disposed inside the observation imaging apparatus 11, the imaging lens 5 is indicated by a broken line in FIGS. 5A and 5B.

As illustrated in FIGS. 5A to 5C, in the observation imaging apparatus 11 according to the present embodiment, the disposed position of the imaging lens 5 in the insertion unit 12 differs from the that of the first embodiment. The imaging lens 5 is disposed in such a manner that a normal line A and an axial principal ray B do not intersect each other (that is, the imaging lens 5 is displaced from the center of an axis in the insertion unit 12). The observation imaging apparatus 11 has a configuration similar to the configuration of the observation imaging apparatus 1 described in the first embodiment except this point. In the present embodiment, only a configuration different from the first embodiment will be described, and common configurations will be designated by like reference signs to omit the description thereof.

[Tilted Disposition of Imaging Lens]

As illustrated in FIGS. 5A to 5C, in the observation imaging apparatus 11, in order to capture an image in the direction inclined with respect to the insertion direction inside a narrow space, the imaging lens 5 is disposed in a tip part 13 of the insertion unit 12 with the imaging direction of the imaging lens 5 tilted with respect to the insertion direction of the insertion unit 12. In other words, when a normal line passing through the center of gravity of a cross section S of the insertion unit 12, the cross section S passing through the center of the effective imaging range of the image sensor 6 and being perpendicular to the insertion direction of the insertion unit 12, is defined as a normal line A, the imaging lens 5 is fixed to the insertion unit 2 in such a manner that an axial principal ray B of the observation subject side surface of a lens L1 is tilted with respect to the normal line A.

In the observation imaging apparatus 1 according to the first embodiment, the imaging lens 5 is disposed in such a manner that the normal line A of the cross section S of the insertion unit 2 and the axial principal ray B intersect each other at the point P. On the other hand, in the observation imaging apparatus 11 according to the present embodiment, as illustrated in FIGS. 5A to 5C, the imaging lens 5 is disposed in such a manner that the normal line A and the axial principal ray B do not intersect each other. Such a disposition makes it easy to dispose, for example, an illumination unit or an operation unit for performing an operation inside a narrow space (both not illustrated in FIGS. 5A to 5C) inside the insertion unit 12 in the observation imaging apparatus 11.

Further, also in the present embodiment, as with the first embodiment, when a point on the axial principal ray B at which the distance between the normal line A and the axial principal ray B is smallest is defined as a point P, the point P is preferably present on the image side relative to the most observation subject side surface of the imaging lens 5 and on the observation subject side relative to the image sensor 6. Since the normal line A and the axial principal ray B do not interest each other in the present embodiment, as illustrated in FIG. 5C, an intersection point between a projective normal line A' obtained by projecting the normal line A onto a plane that includes the axial principal ray B and is parallel to the normal line A and the axial principal ray B is defined as the point P.

Further, in the present embodiment, with regard to the tilt of the imaging lens 5 in the imaging direction with respect to the insertion direction of the insertion unit 12, the angle between the axial principal ray B and the projective normal line A' is defined as the angle α as illustrated in FIG. 5C.

When the imaging lens 5 is disposed with the imaging direction thereof tilted so that the point P on the axial principal ray B is present on the observation subject side relative to the image sensor 6, it is possible to efficiently dispose the imaging lens 5 while reducing a gap with respect to the size of the insertion unit 12.

EXAMPLES

Next, the configuration of the imaging lens 5 which is disposed in the tip part 3 of the observation imaging apparatuses 1, 11 according to the present invention will be specifically described by showing examples. However, the present invention is not limited to the following examples. Note that each example will be described with the disposition relationship of the imaging lens 5 in the observation imaging apparatus 1 according to the first embodiment described above. An optical system (imaging lens 5) described in each example described below is an observation optical system as an imaging optical system used in an imaging apparatus (optical apparatus) such as a digital camera or a video camera, and can be preferably applied to an observation imaging apparatus for observing the inside of a narrow space, such as a microscope or an endoscope. Further, in each lens sectional view, the left side of the drawing corresponds to the observation subject side (object side), and the right side corresponds to the image plane side.

Example 1

Figure 6:
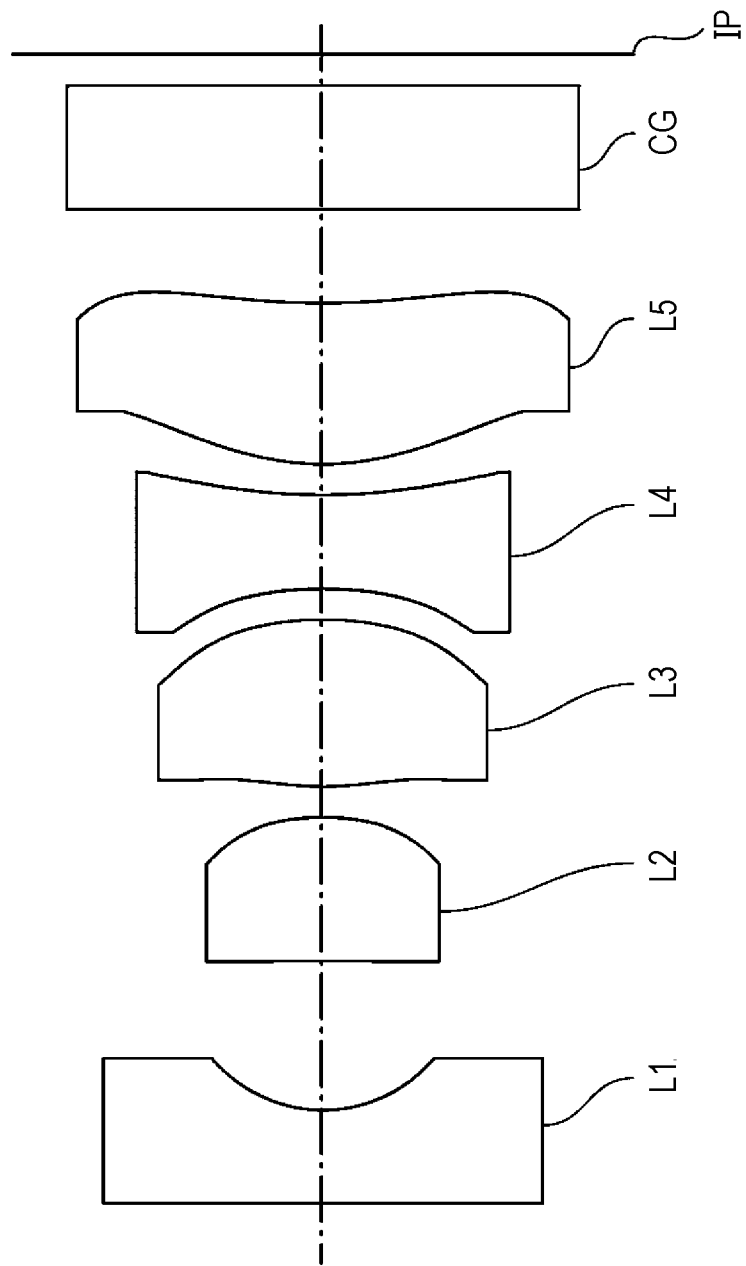
FIG. 6 is a sectional view illustrating a lens configuration of an imaging lens according to Example 1 of the present invention.

First, an imaging lens according to Example 1 of the present invention will be described with reference to FIG. 6. FIG. 6 is a sectional view illustrating the lens configuration of the imaging lens according to Example 1 of the present invention.

The imaging lens includes a first lens L1 having negative refractive power, a second lens L2 having positive refractive power, a third lens L3 having positive refractive power, a fourth lens L4 having negative refractive power, and a fifth lens L5 having positive refractive power which are disposed in this order from the observation subject side. An aperture stop is disposed on the object side surface of the second lens L2.

Hereinbelow, the shape of each lens will be described. The first lens L1 is a plano-concave lens whose image side surface has a concave shape. The second lens L2 is a biconvex lens. The third lens L3 is a biconvex lens. The fourth lens L4 is a biconcave lens. The fifth lens L5 is a meniscus lens whose object side has a convex shape. Further, in Example 1, all of the first to fifth lenses L1 to L5 are resin lenses.

As shown in Table 7, the imaging lens of Example 1 is disposed in the insertion unit of the observation imaging apparatus, the insertion unit having a length L and a diameter DI, with α=45°, and the image sensor is disposed with γ=0°. Note that the disposition of the imaging lens and the image sensor is not limited thereto. For example, the imaging lens may be disposed with α=30° or α=20°, and the image sensor may be disposed with γ=5° or γ=10°. The same applies to each example described below.

Further, "IP" in FIG. 6 is an imaging plane on which the image sensor 6 is disposed. A parallel plate having substantially no refractive power, such as a cover glass, is disposed on the object side of the imaging plane IP. These points also apply to lens sectional views in the other examples. Thus, description thereof will be omitted below.

Table 1 shows surface data of the imaging lens of Example 1. In Table 1, "SURFACE NUMBER" is the order of a lens surface counted from the object side, "r" is the radius of curvature of the lens surface, "d" is the distance of the lens surface on the optical axis, "nd" is the refractive power with respect to the d-line, and "vd" is the Abbe number with respect to the d-line. Further, "*" affixed to the surface number indicates that the lens surface has an aspherical shape, and "S" denotes the aperture stop. Further, "∞" of the radius of curvature represents a plane. In each table, the unit of length is "mm", and the unit of angle is "°".

Table 2 shows the aspherical coefficient of each aspherical surface. The aspherical coefficient is a value when each aspherical shape is defined by the following expression. Further, Table 7 shows a specification value of each example. Table 8 shows a numerical value of each conditional expression. In Table 7, fL1 to fL7 represent focal lengths of the first to seventh lenses L1 to L7, respectively.

$$X(Y)=CY^2/[1+\{1-(1+K)\cdot C^2 Y^2\}^{1/2}]+A4\cdot Y^4+A6\cdot Y^6+A8\cdot Y^8+A10\cdot Y^{10}+A12\cdot Y^{12}$$

In Table 6, "E-a" represents "×10−a". Further, in the above expression, "X" is a displaced amount from a reference plane in the optical axis direction, "C" is a curvature on the vertex of the surface, "Y" is a height from the optical axis in the direction perpendicular to the optical axis, "K" is the Korenich coefficient, and "An" is an n-th order aspherical coefficient.

The above matters relating to these tables also apply to each table described in the other examples. Thus, description thereof will be omitted below.

TABLE 1

| SURFACE NUMBER | r | d | nd | vd |
|---|---|---|---|---|
| OBJECT SURFACE | ∞ | 4.000 | | |
| 1 | ∞ | 0.300 | 1.5439 | 55.88 |
| 2* | 0.471 | 0.481 | | |
| 3S* | 50.000 | 0.462 | 1.5439 | 55.88 |
| 4* | −0.888 | 0.100 | | |
| 5* | 0.998 | 0.537 | 1.5439 | 55.88 |
| 6* | −1.038 | 0.100 | | |
| 7* | −1.153 | 0.300 | 1.6613 | 20.37 |
| 8* | 1.945 | 0.100 | | |
| 9* | 0.889 | 0.520 | 1.5439 | 55.88 |
| 10* | 2.618 | 0.300 | | |
| 11 | ∞ | 0.400 | 1.5168 | 64.20 |
| 12 | ∞ | 0.100 | | |

TABLE 2

| SURFACE NUMBER | k | A4 | A6 | A8 | A10 | A12 | A14 |
|---|---|---|---|---|---|---|---|
| 2 | −0.8309 | 1.2183E+0 | 8.2912E−1 | 3.6335E+1 | −1.5379E+2 | −2.2706E−6 | −5.3398E−7 |
| 3 | −10.0000 | −2.1240E+0 | −5.8410E+0 | −1.9426E+2 | 1.4864E+3 | 3.0895E−8 | 2.0113E−8 |
| 4 | 2.6644 | −4.2369E+0 | 2.3617E+1 | −1.2639E+2 | 3.2341E+2 | 8.2325E+1 | −3.0036E+2 |
| 5 | −10.0000 | −2.5307E+0 | 1.1856E+1 | −6.5833E+1 | 1.6942E+2 | −1.5505E+0 | 1.7853E+1 |
| 6 | 0.3041 | 3.2582E−2 | −1.0323E+1 | 3.6643E+1 | −4.8778E+1 | 5.3768E+1 | −2.7661E+1 |
| 7 | 3.8680 | 3.4322E−1 | −5.1402E+0 | 3.2049E+0 | 6.3361E+1 | 4.7353E+0 | −8.0984E+0 |
| 8 | 2.9990 | −1.2469E−1 | 2.9578E−1 | −4.0516E+0 | 9.8905E+0 | −5.6130E+0 | 8.7334E−1 |
| 9 | −1.9225 | −1.7729E−1 | −8.0408E−2 | 5.8687E−1 | −2.1235E+0 | 1.2649E+0 | −1.3398E+0 |
| 10 | −0.8546 | −2.2301E−2 | −1.3362E+0 | 3.3310E+0 | −5.8360E+0 | 4.1433E+0 | −9.2867E−1 |

Figure 7:
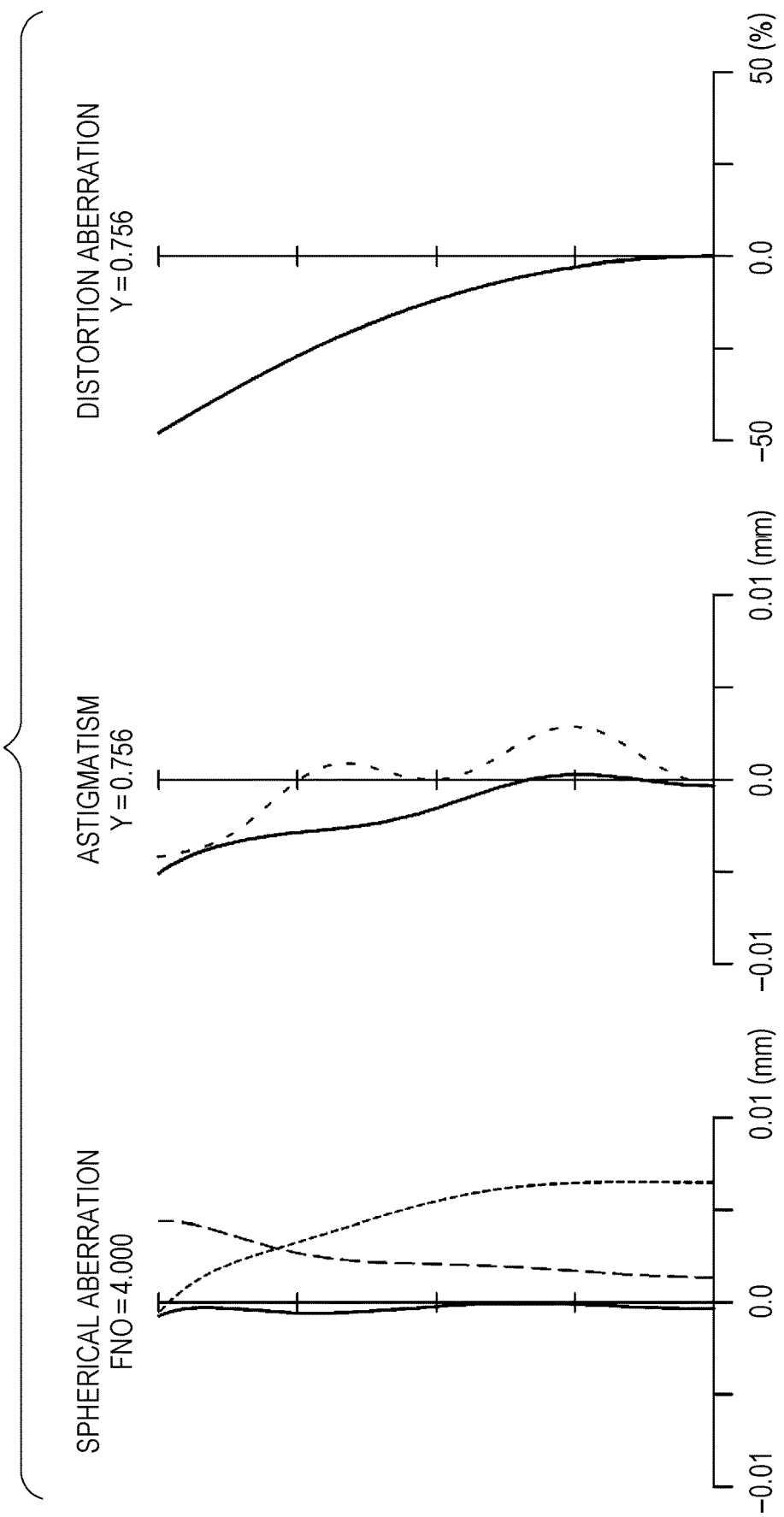
FIG. 7 is a longitudinal aberration diagram illustrating longitudinal aberration of the imaging lens according to Example 1 of the present invention.

Further, FIG. 7 illustrates a longitudinal aberration diagram of the imaging lens of Example 1. The longitudinal aberration diagram shows spherical aberration (mm), astigmatism (mm), and distortion aberration (%) in this order from the left side of the drawing. In the diagram showing the spherical aberration, the vertical axis represents the F number, and the horizontal axis represents defocus. Further, a solid line represents spherical aberration at the d-line (wavelength λ=587.6 nm), a long broken line represents spherical aberration at the C-line (wavelength λ=656.3 nm), and a short broken line represents spherical aberration at the g-line (wavelength λ=435.8 nm). In the diagram showing the astigmatism, the vertical axis represents the image height, and the horizontal axis represents defocus. Further, a solid line represents a sagittal plane with respect to the d-line, and a broken line represents a meridional section with respect to the d-line. In the diagram showing the distortion aberration, the vertical axis represents the image height, and the horizontal axis represents %. These matters relating to the longitudinal aberration diagram also apply to the longitudinal aberration diagrams in the other examples. Thus, the description thereof will be omitted below.

Example 2

Figure 8:
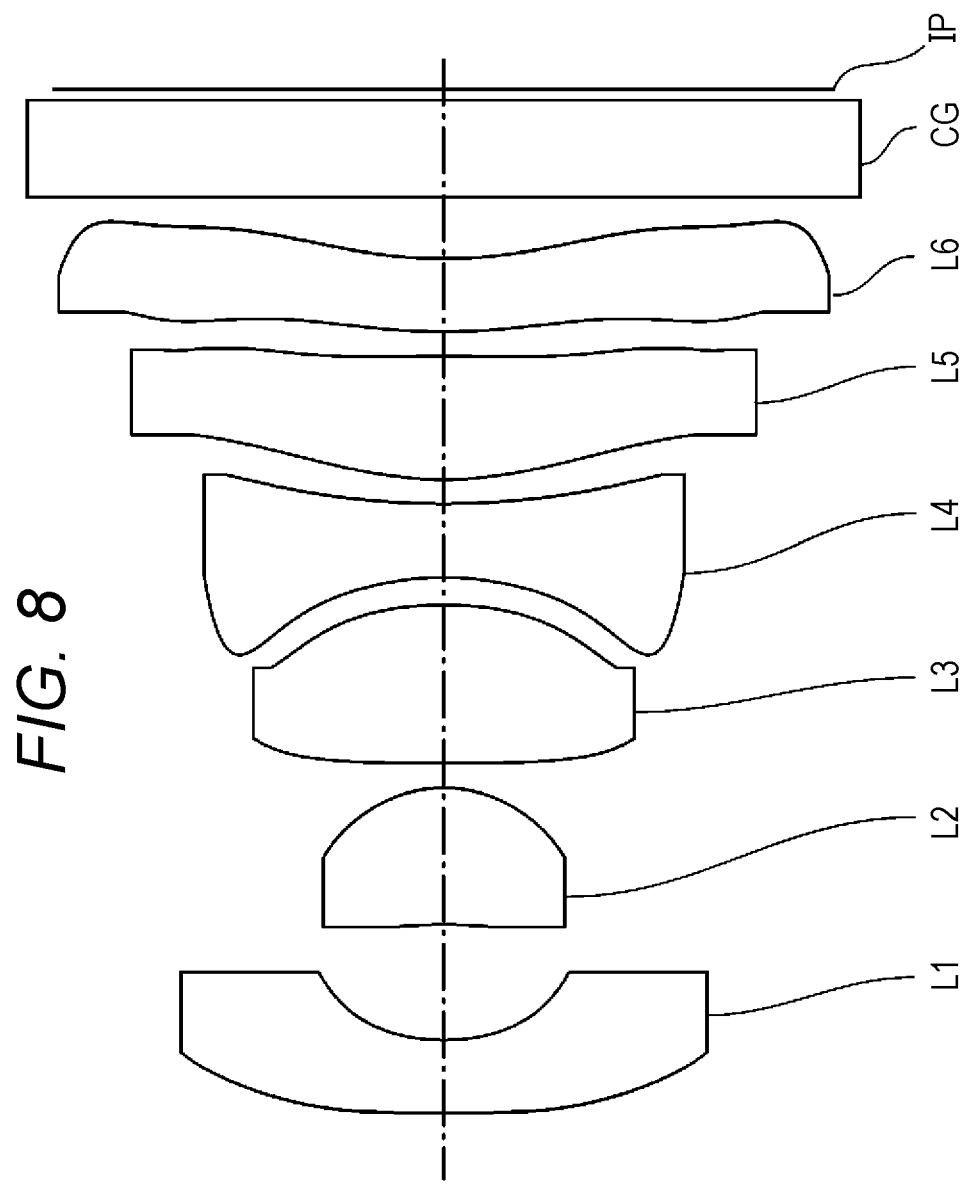
FIG. 8 is a sectional view illustrating a lens configuration of an imaging lens according to Example 2 of the present invention.
Figure 9:
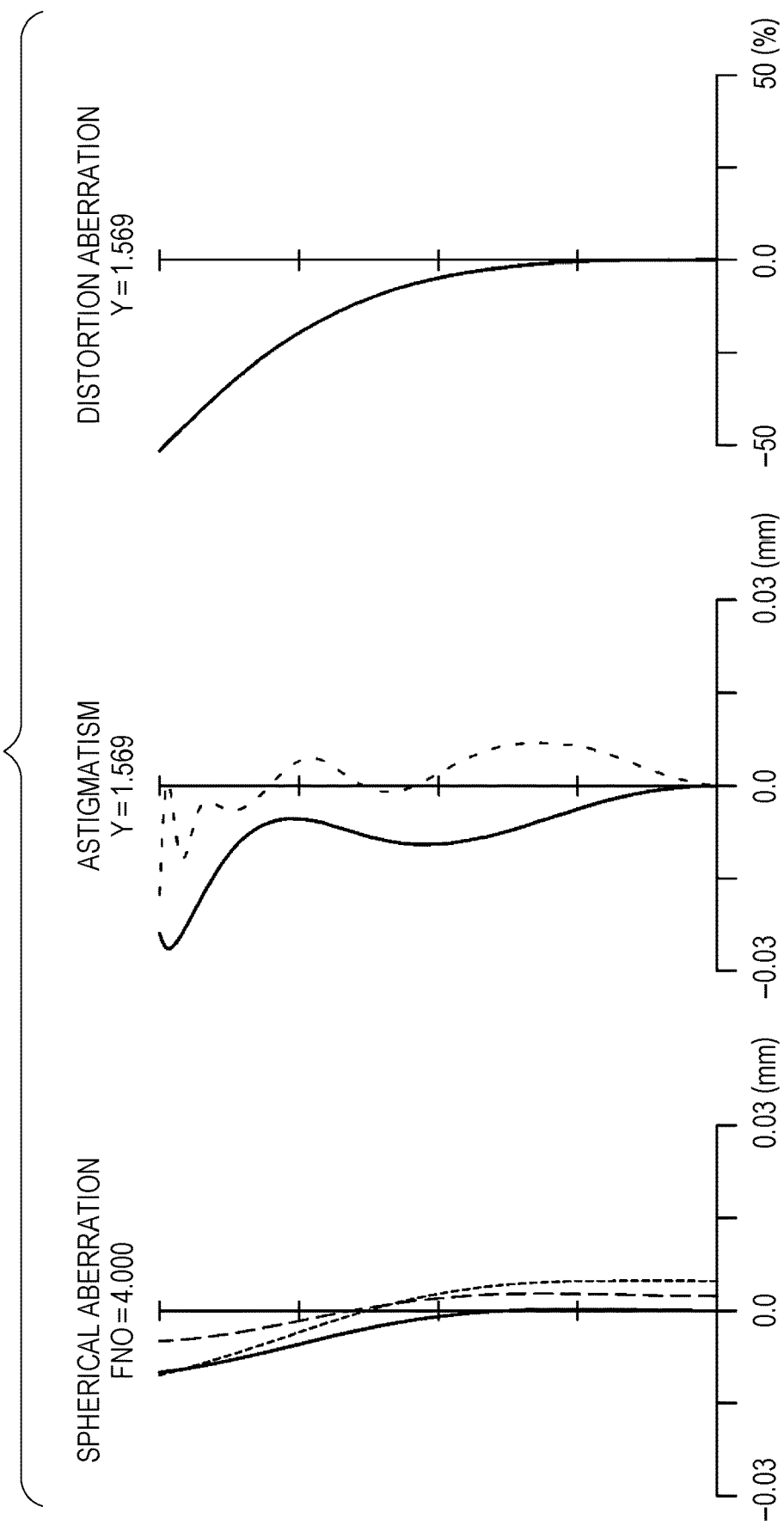
FIG. 9 is a longitudinal aberration diagram illustrating longitudinal aberration of the imaging lens according to Example 2 of the present invention.

Next, an imaging lens according to Example 2 of the present invention will be described with reference to FIGS. 8 and 9. FIG. 8 is a sectional view illustrating the lens configuration of the imaging lens according to Example 2 of the present invention. FIG. 9 is a longitudinal aberration diagram of the imaging lens according to Example 2.

The imaging lens includes a first lens L1 having negative refractive power, a second lens L2 having positive refractive power, a third lens L3 having positive refractive power, a fourth lens L4 having negative refractive power, a fifth lens L5 having positive refractive power, and a sixth lens L6 having negative refractive power which are disposed in this order from the observation subject side. An aperture stop is disposed on the object side surface of the second lens L2.

Hereinbelow, the shape of each lens will be described. The first lens L1 is a meniscus lens whose object side surface has a convex shape. The second lens L2 is a meniscus lens having a shape convex to the image side. The third lens L3 is a biconvex lens. The fourth lens L4 is a biconcave lens. The fifth lens L5 is a biconvex lens. The sixth lens L6 is a meniscus lens having a shape convex to the object side. Further, in Example 2, all of the first to sixth lenses L1 to L6 are resin lenses.

The imaging lens of Example 2 is disposed in the insertion unit of the observation imaging apparatus shown in Table 7, the insertion unit having a length L and a diameter DI, with α=45°, and the image sensor is disposed with γ=0°.

Table 3 shows surface data of the imaging lens of Example 2. Table 4 shows an aspherical coefficient of each aspherical surface.

TABLE 3

| SURFACE NUMBER | r | d | nd | vd |
|---|---|---|---|---|
| OBJECT SURFACE | ∞ | 8.000 | | |
| 1* | 30.000 | 0.300 | 1.5439 | 55.88 |
| 2* | 0.827 | 0.473 | | |
| 3S* | −2.380 | 0.561 | 1.5439 | 55.88 |
| 4* | −0.543 | 0.100 | | |
| 5* | 8.108 | 0.651 | 1.5439 | 55.88 |
| 6* | −1.387 | 0.112 | | |
| 7* | −1.179 | 0.300 | 1.6510 | 21.51 |
| 8* | 3.059 | 0.100 | | |
| 9* | 1.494 | 0.508 | 1.5439 | 55.88 |

TABLE 3-continued

| SURFACE NUMBER | r | d | nd | vd |
|---|---|---|---|---|
| 10* | −8.114 | 0.100 | | |
| 11* | 2.383 | 0.300 | 1.6510 | 21.51 |
| 12* | 1.983 | 0.251 | | |
| 13 | ∞ | 0.400 | 1.5168 | 64.20 |
| 14 | ∞ | 0.045 | | |

TABLE 4

| SURFACE NUMBER | K | A4 | A6 | A8 | A10 | A12 | A14 |
|---|---|---|---|---|---|---|---|
| 1 | −0.2985 | 3.6738E−1 | −2.7189E−1 | 4.5988E−2 | 3.6446E−2 | −7.1519E−4 | −6.8962E−10 |
| 2 | 1.0552 | 4.6778E−1 | 2.1923E+0 | −1.8925E−1 | −1.0891E+1 | −8.2460E−9 | −6.9953E−10 |
| 3 | 8.8450 | −1.1689E+0 | −2.5852E+0 | −4.5606E+1 | 2.9636E+2 | 1.0709E−10 | 2.4216E−11 |
| 4 | −0.1644 | 1.4897E−1 | −5.5923E−1 | 8.4186E+0 | −2.9357E+1 | 2.9867E−1 | −3.9230E−1 |
| 5 | 10.0000 | −1.0083E−1 | 6.3686E−1 | −5.3806E−1 | 3.7073E−1 | −5.6252E−3 | 2.3317E−2 |
| 6 | 1.7458 | −1.7867E−1 | −7.9140E−1 | 1.7299E+0 | 3.3824E−1 | 1.9507E−1 | −3.6127E−2 |
| 7 | −7.3384 | −1.5339E−1 | −6.4502E−1 | −3.1011E−1 | 1.4718E+0 | 1.7179E−2 | −1.0577E−2 |
| 8 | 8.4411 | −1.5865E−1 | 3.0286E−1 | −2.9291E−1 | 1.0399E−2 | −1.9892E−3 | 1.1407E−3 |
| 9 | −2.5729 | −1.2114E−1 | −4.5848E−2 | 1.0068E−1 | −4.5891E−2 | 4.5724E−3 | −1.7739E−3 |
| 10 | −6.2993 | 3.8951E−1 | −4.0341E−1 | 6.7872E−2 | 3.1183E−2 | 5.7659E−3 | −1.2141E−3 |
| 11 | 0.5240 | −2.2868E−1 | −3.7872E−2 | 1.0667E−1 | −2.1951E−2 | 1.5472E−3 | −2.4186E−3 |
| 12 | 0.1204 | −4.8331E−2 | −2.4289E−1 | 1.8472E−1 | −3.7645E−2 | −6.1259E−4 | −2.9985E−4 |

Example 3

Figure 10:
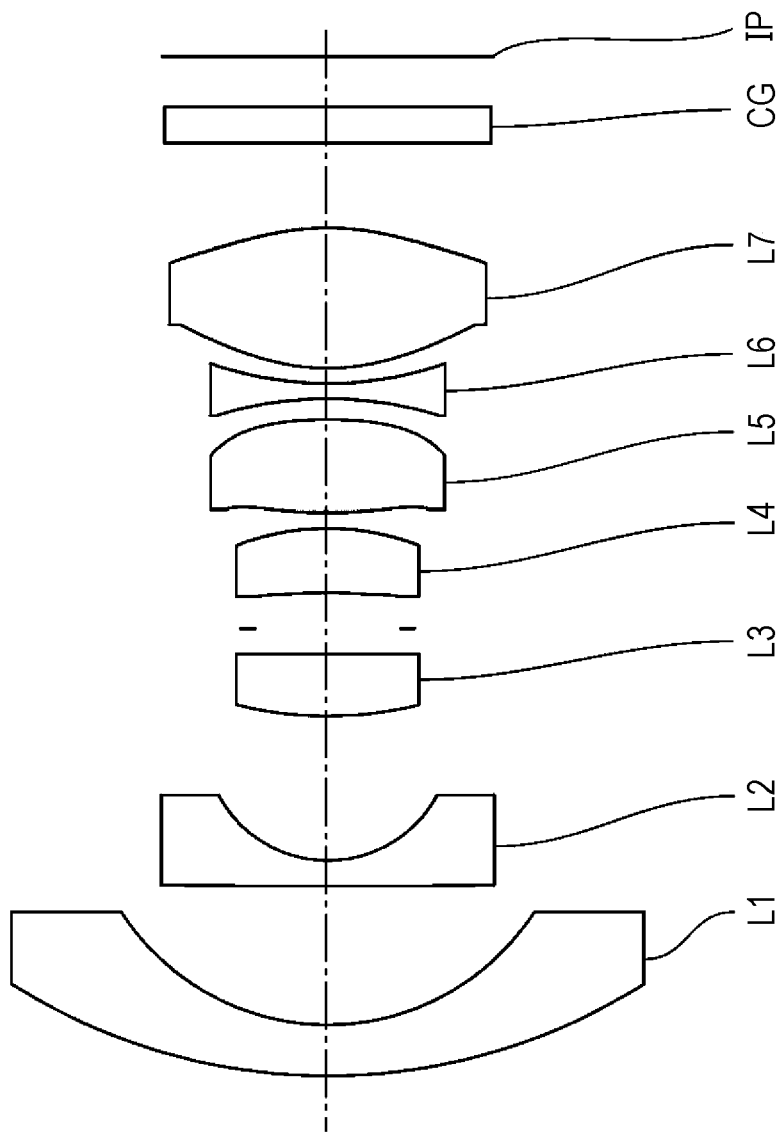
FIG. 10 is a sectional view illustrating a lens configuration of an imaging lens according to Example 3 of the present invention.
Figure 11:
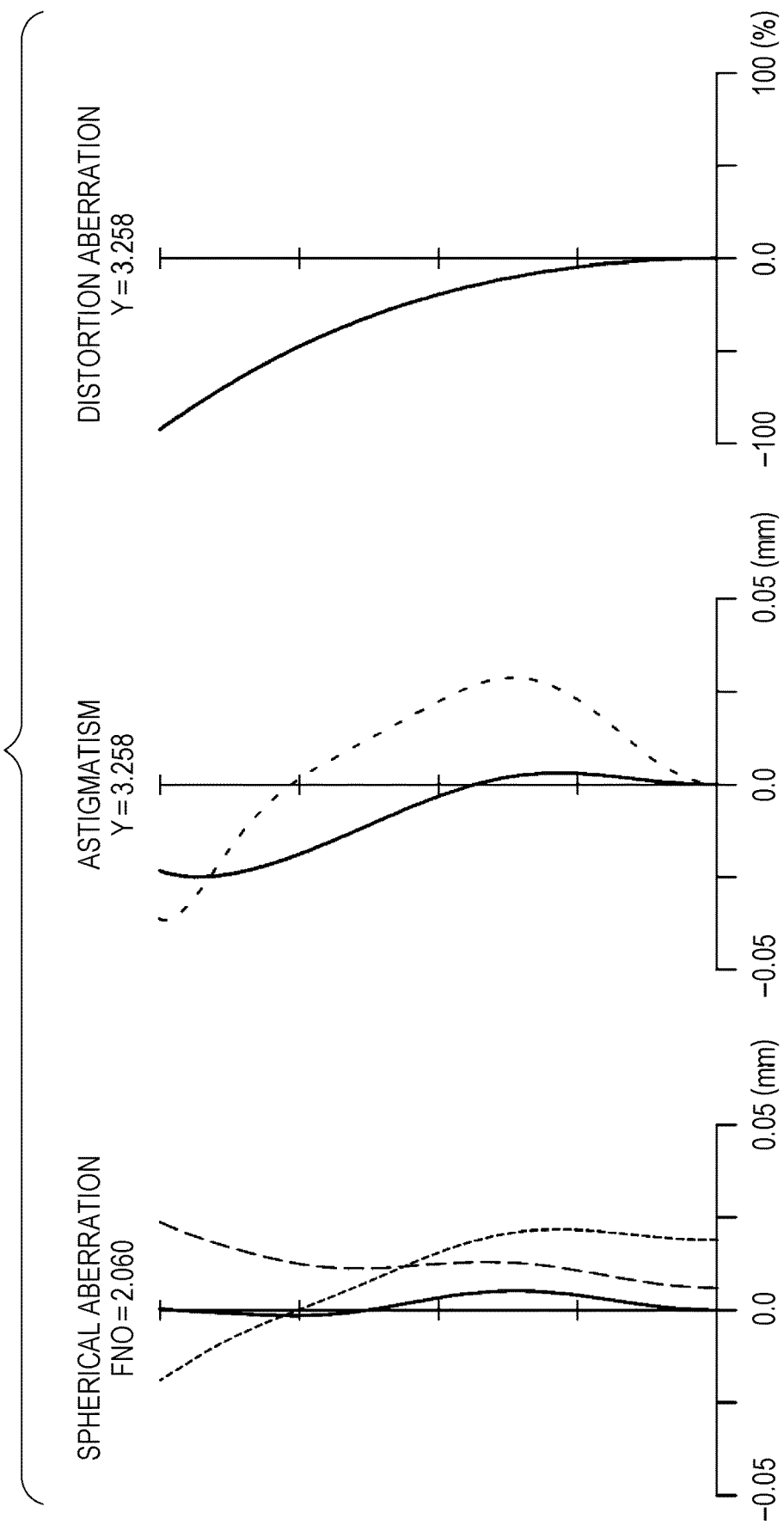
FIG. 11 is a longitudinal aberration diagram illustrating longitudinal aberration of the imaging lens according to Example 3 of the present invention.

Next, an imaging lens according to Example 3 of the present invention will be described with reference to FIGS. 10 and 11. FIG. 10 is a sectional view illustrating the lens configuration of the imaging lens according to Example 3 of the present invention. FIG. 11 is a longitudinal aberration diagram of the imaging lens according to Example 3.

The imaging lens includes a first lens L1 having negative refractive power, a second lens L2 having negative refractive power, a third lens L3 having positive refractive power, a fourth lens L4 having positive refractive power, a fifth lens L5 having positive refractive power, a sixth lens L6 having negative refractive power, and a seventh lens L7 having positive refractive power which are disposed in this order from the observation subject side. An aperture stop is disposed between the third lens L3 and the fourth lens L4.

Hereinbelow, the shape of each lens will be described. The first lens L1 is a meniscus lens whose object side surface has a convex shape. The second lens L2 is a meniscus lens having a shape convex to the object side. The third lens L3 is a meniscus lens having a shape convex to the object side. The fourth lens L4 is a meniscus lens having a shape convex to the image side. The fifth lens L5 is a biconvex lens. The sixth lens L6 is a biconcave lens. The seventh lens L7 is a biconvex lens. Further, in Example 3, two lenses, specifically, the firth lens L5 and the seventh lens L7 are resin lenses.

The imaging lens of Example 3 is disposed in the insertion unit of the observation imaging apparatus shown in Table 7, the insertion unit having a length L and a diameter DI, with α=450, and the image sensor is disposed with γ=00.

Table 5 shows surface data of the imaging lens of Example 3. Table 6 shows an aspherical coefficient of each aspherical surface.

TABLE 5

| SURFACE NUMBER | r | d | nd | vd |
|---|---|---|---|---|
| OBJECT SURFACE | ∞ | ∞ | | |
| 1 | 11.706 | 1.000 | 1.9537 | 32.32 |
| 2 | 4.850 | 2.727 | | |
| 3 | 415.404 | 0.500 | 1.5688 | 56.04 |
| 4 | 2.456 | 2.832 | | |
| 5 | 7.536 | 1.218 | 1.9537 | 32.32 |
| 6 | 275.631 | 0.500 | | |
| 7S | ∞ | 0.700 | | |
| 8 | −15.181 | 1.272 | 1.8830 | 40.81 |
| 9 | −4.955 | 0.300 | | |
| 10* | 7.850 | 1.821 | 1.5533 | 71.68 |
| 11* | −8.471 | 0.413 | | |
| 12 | −7.415 | 0.300 | 2.0027 | 19.31 |
| 13 | 7.008 | 0.300 | | |
| 14* | 4.093 | 2.749 | 1.5533 | 71.68 |
| 15* | −5.025 | 1.668 | | |
| 16 | ∞ | 0.700 | 1.5168 | 64.20 |
| 17 | ∞ | 1.000 | | |

TABLE 6

| SURFACE NUMBER | k | A4 | A6 | A8 | A10 | A12 | A14 |
|---|---|---|---|---|---|---|---|
| 10 | −8.6873 | −3.4428E−3 | 5.1418E−6 | −7.7574E−4 | 2.1516E−4 | −3.1262E−5 | 0.0000E+0 |
| 11 | 5.4719 | −8.0609E−3 | 3.2449E−5 | −2.9764E−4 | 5.7982E−5 | −5.3481E−6 | 0.0000E+0 |
| 14 | −7.6567 | 6.1786E−3 | −8.8641E−4 | 1.0347E−4 | −7.7893E−6 | 2.2764E−7 | 0.0000E+0 |
| 15 | −7.0835 | −2.4097E−3 | 5.3792E−4 | −1.4962E−5 | −2.6757E−6 | 1.0881E−7 | 0.0000E+0 |

TABLE 7

SPECIFICATION TABLE

|  | EXAMPLE 1 | EXAMPLE 2 | EXAMPLE 3 |
|---|---|---|---|
| Fno | 4.000 | 4.000 | 2.060 |
| f | 0.816 | 1.120 | 2.245 |
| β | 60.000 | 68.798 | 87.000 |
| PIT (mm) | 0.0014 | 0.0014 | 0.0050 |
| L | 200.00 | 200.000 | 200.000 |
| DI | φ6.000 | φ6.000 | φ19.000 |
| Dm (mm$^2$) | 4.064 | 4.064 | 58.080 |
| Ds (mm$^2$) | 28.274 | 28.274 | 283.529 |
| OAL | 3.700 | 4.201 | 20.000 |
| YY | 3.084 | 3.084 | 11.000 |
| fL1 | −0.866 | −1.570 | −9.349 |
| fL2 | 1.610 | 1.169 | −4.345 |
| fL3 | 1.031 | 2.231 | 8.106 |
| fL4 | −1.054 | −1.272 | 7.871 |
| fL5 | 2.239 | 2.363 | 7.668 |
| fL6 | — | −25.721 | −3.556 |
| fL7 | — | — | 4.567 |

Table 8 shows values of the conditional expressions (1) to (11) in each example.

TABLE 8

| CONDITIONAL EXPRESSION | EXAMPLE 1 | EXAMPLE 2 | EXAMPLE 3 |
|---|---|---|---|
| (1) | 0.144 | 0.144 | 0.205 |
| (2) | −1.062 | −1.402 | −4.165 |
| (3) | 1.859 | 0.745 | 0.867 |
| (4) | 1.661 | 1.651 | 1.553 |
| (5) | 1.200 | 1.362 | 1.818 |
| (6) | 1.062 | 1.044 | 2.035 |
| (7) | 550.714 | 550.714 | 1067.961 |
| (8) | 54.047 | 47.604 | 10.000 |
| (9) | 0.268 | 0.441 | 0.900 |
| (10) | 0.800 | 0.859 | 1.154 |
| (11) | 0.000 | 0.000 | 0.000 |

As described above, the present invention, for example, has a high resolution and can be preferably used in observation of the inside of a narrow space where the human cannot directly enter. Further, the observation imaging apparatus according to the present invention is suitable for observation of a fine subject by a microscope.

What is claimed is:

1. An endoscopic observation imaging apparatus comprising:
   an insertion unit having a tubular shape;
   an imaging optical system disposed in a tip part of the insertion unit, having no intermediate imaging plane, and including one or more lenses;
   an image sensor configured to convert an optical image formed by the imaging optical system on an image side of the imaging optical system to an electric signal, wherein
   a normal line defined as normal line A passes through a center of gravity of a cross section S of the insertion unit, the cross section S passing through a center of an effective imaging range of the image sensor and being perpendicular to an insertion direction of the insertion unit,
   the imaging optical system is fixed to the insertion unit in such a manner that an axial principal ray B of an observation subject side surface of a lens L1 disposed on the observation subject side of the imaging optical system closest to an observation subject is tilted with respect to the normal line A,
   a point P on the axial principal ray B at which a distance between the normal line A and the axial principal ray B is smallest is located on the image side relative to the observation subject side surface of the lens L1 and on the observation subject side relative to the image sensor, and in a case where the axial principal ray B and the normal line A intersect each other at an intersecting point, the point P is located at the intersecting point, and
   the observation imaging apparatus satisfies the following expression:

$$0.10 < Dm/Ds < 0.80 \qquad (1)$$

where
   Dm is an area of the effective imaging range of the image sensor, and
   Ds is an area of the cross section S.

2. The endoscopic observation imaging apparatus according to claim 1, wherein the imaging optical system does not include any optical elements having a reflecting surface.

3. The endoscopic observation imaging apparatus according to claim 1, wherein the imaging optical system includes five or more lenses.

4. The endoscopic observation imaging apparatus according to claim 1, wherein the observation imaging apparatus satisfies the following expression:

$$-50.00 < fL1/f < -0.01 \qquad (2)$$

where
fL1 is a focal length of the lens L1, and
f is a focal length of the imaging optical system.

5. The endoscopic observation imaging apparatus according to claim 1, wherein
   the imaging optical system includes a lens L2 having positive refractive power on the image side of the lens L1, and
   the observation imaging apparatus satisfies the following expression:

$$0.02 < fL2/|fL1| < 20.00 \qquad (3)$$

where
fL1 is a focal length of the lens L1, and
fL2 is a focal length of the lens L2 having positive refractive power.

6. The endoscopic observation imaging apparatus according to claim 1, wherein
   the imaging optical system includes at least one lens N having negative refractive power on the image side relative to the lens L1, and
   the observation imaging apparatus satisfies the following expression:

$$1.500 < NdN < 2.200 \qquad (4)$$

where
NdN is a refractive index of the lens N at the d-line.

7. The endoscopic observation imaging apparatus according to claim 1, wherein the observation imaging apparatus satisfies the following expression:

$$0.2 < OAL/YY < 10.0 \qquad (5)$$

where
OAL is a distance from a lens surface on the observation subject side of the imaging optical system closest to an observation subject, to the image sensor, and
YY is an effective diagonal length of the image sensor.

8. The endoscopic observation imaging apparatus according to claim 1, wherein the imaging optical system includes at least one lens made of resin, and the observation imaging apparatus satisfies the following expression:

$$0.30 < |fLP|/f < 10.00 \tag{6}$$

where fLP is a focal length of the lens made of resin, and f is a focal length of the imaging optical system.

9. The endoscopic observation imaging apparatus according to claim 1, wherein the observation imaging apparatus satisfies the following expression:

$$20.0 < YY/PIT/Fno < 800.0 \tag{7}$$

where

YY is an effective diagonal length of the image sensor,

PIT is a pixel pitch of the image sensor, and

Fno is an F number of the imaging optical system.

10. The endoscopic observation imaging apparatus according to claim 1, wherein the insertion unit includes a tubular member extending in the insertion direction, and the observation imaging apparatus satisfies the following expression:

$$2.0 < L/OAL \tag{8}$$

where

L is a length of the insertion unit in the insertion direction, and

OAL is a distance from a lens surface on the observation subject side of the imaging optical system closest to an observation subject, to an imaging plane.

11. The endoscopic observation imaging apparatus according to claim 1, wherein the observation imaging apparatus satisfies the following expression:

$$0.00 \leq \tan(|\beta| - |\alpha|) < 2.00 \tag{9}$$

where

α is an angle between the normal line A and the axial principal ray B, and

β is a half angle of view of a principal ray of an outermost off-axis light flux of the imaging optical system.

12. The endoscopic observation imaging apparatus according to claim 1, wherein the observation imaging apparatus satisfies the following expression:

$$0.01 < (OAL \times \sin|\alpha| + YY \times \cos|\alpha|)/DI < 5.00 \tag{10}$$

where

OAL is a distance from a lens surface on the observation subject side of the imaging optical system closest to an observation subject, to an imaging plane, α is an angle between the normal line A and the axial principal ray B, YY is an effective diagonal length of the image sensor, and DI is a diameter of a circumcircle of the cross section S.

13. The endoscopic observation imaging apparatus according to claim 1, wherein the effective imaging range of the image sensor has a substantially rectangular shape, and the observation imaging apparatus satisfies the following expression:

$$0.00 \leq \tan|\gamma| < 0.60 \tag{11}$$

where

γ is an angle between a plane formed by an angle α between the normal line A and the axial principal ray B and the axial principal ray B and a lateral direction of the effective imaging range of the image sensor.

14. The endoscopic observation imaging apparatus according to claim 1, further comprising an illumination unit for illuminating the observation subject in a tip of the insertion unit, wherein the axial principal ray B and an orientational axis illuminated by the illumination unit are substantially parallel to each other.

15. The endoscopic observation imaging apparatus according to claim 1, further comprising an image processing unit configured to electrically process image data captured by the image sensor to correct distortion of an image.

16. The endoscopic observation imaging apparatus according to claim 1, wherein the imaging optical system is attached rotatably about the normal line A, and the observation imaging apparatus further comprises an image processing unit configured to combine images captured by the image sensor while rotating the imaging optical system.

* * * * *